(12) United States Patent
Nishide et al.

(10) Patent No.: US 7,492,854 B2
(45) Date of Patent: Feb. 17, 2009

(54) X-RAY CT IMAGING METHOD AND X-RAY CT APPARATUS

(75) Inventors: Akihiko Nishide, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/557,716

(22) Filed: Nov. 8, 2006

(65) Prior Publication Data

US 2007/0110209 A1  May 17, 2007

(30) Foreign Application Priority Data

Nov. 11, 2005  (JP) .............................. 2005-327266

(51) Int. Cl.
*G01N 23/00* (2006.01)

(52) U.S. Cl. ......................................................... 378/4

(58) Field of Classification Search ...................... 378/4, 378/207, 901
See application file for complete search history.

(56) References Cited

U.S. PATENT DOCUMENTS

| | | | | |
|---|---|---|---|---|
| 4,105,922 A | * | 8/1978 | Lambert et al. | ............. 382/131 |
| 4,856,528 A | * | 8/1989 | Yang et al. | .................. 382/131 |
| 4,872,188 A | * | 10/1989 | Lauro et al. | .................... 378/62 |
| 5,034,969 A | * | 7/1991 | Ozaki | ........................... 378/18 |
| 5,128,864 A | * | 7/1992 | Waggener et al. | ............. 378/14 |
| 5,287,276 A | * | 2/1994 | Crawford et al. | ................ 378/4 |
| 5,452,337 A | * | 9/1995 | Endo et al. | ...................... 378/4 |
| 5,528,644 A | * | 6/1996 | Ogawa et al. | ................... 378/8 |

(Continued)

FOREIGN PATENT DOCUMENTS

JP     2004-073360     3/2004

(Continued)

OTHER PUBLICATIONS

Hounsfield Scale, Wikipedia [Online], Aug. 29, 2007, retrieved from http://en.wikipedia.org/wiki/Hounsfield_scale.

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

The present invention provides the adjustment of CT value which is the pixel value of a tomographic image in the conventional scan (axial scan) or cinescan or helical scan by an X-ray CT apparatus incorporating a multi column X-ray detector or a two-dimensional X-ray detector of matrix arrangement represented by a flat panel X-ray detector. The gain and bias of the projection data of each row are adjusted prior to the three-dimensional back projection or prior to the reconstruction function convolution. Alternatively, the gain and bias are adjusted after determining the gain and bias value to adjust the CT value by taking into account the contribution rate of each row to the tomographic image after the three-dimensional back projection. Alternatively, the gain and bias are adjusted after determining the gain and bias value to adjust CT value by taking into account the contribution rate of each row to the tomographic image relying on the position of each row in z direction in case of axial scan after three-dimensional back projection.

14 Claims, 17 Drawing Sheets

U.S. PATENT DOCUMENTS

| | | | |
|---|---|---|---|
| 6,078,638 A * | 6/2000 | Sauer et al. | 378/4 |
| 6,188,744 B1 * | 2/2001 | Shinohara et al. | 378/8 |
| 6,201,849 B1 | 3/2001 | Lai | |
| 6,337,992 B1 * | 1/2002 | Gelman | 600/425 |
| 6,400,789 B1 * | 6/2002 | Dafni | 378/15 |
| 6,658,081 B2 * | 12/2003 | Bruder et al. | 378/15 |
| 6,782,071 B1 * | 8/2004 | Tsuyuki | 378/4 |
| 6,845,144 B2 | 1/2005 | Nishide et al. | |
| 6,865,247 B2 | 3/2005 | Hagiwara | |
| 2004/0116796 A1 * | 6/2004 | Li | 600/407 |
| 2004/0223583 A1 * | 11/2004 | Tsujii | 378/19 |
| 2007/0147580 A1 * | 6/2007 | Wu et al. | 378/18 |

FOREIGN PATENT DOCUMENTS

| | | | |
|---|---|---|---|
| JP | 2005253841 A * | 9/2005 | |
| WO | 9836691 A1 | 8/1998 | |

OTHER PUBLICATIONS

Kak et al., "Principles of Computerized Tomographic Imaging: Chapter 3", Principles of Computerized Tomographic Imaging, IEEE Press, New York, NY, US, 1999, pp. 49-112.

Netherlands Search Report dated Aug. 30, 2007, for GE Medical Systems Global Technology Company, LLC, Application No. NL 1032848.

* cited by examiner

Flow of Object Imaging

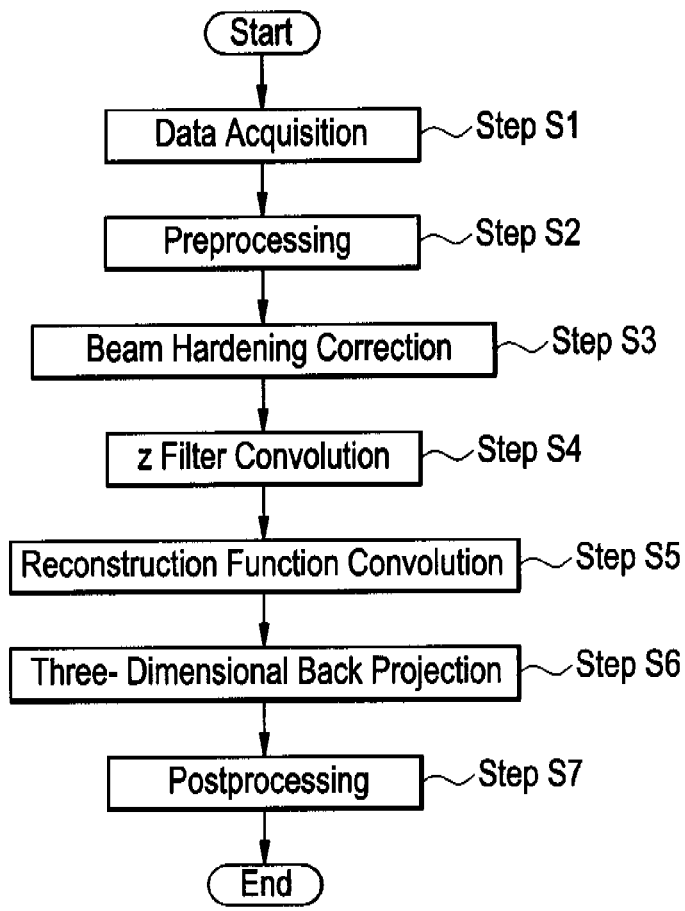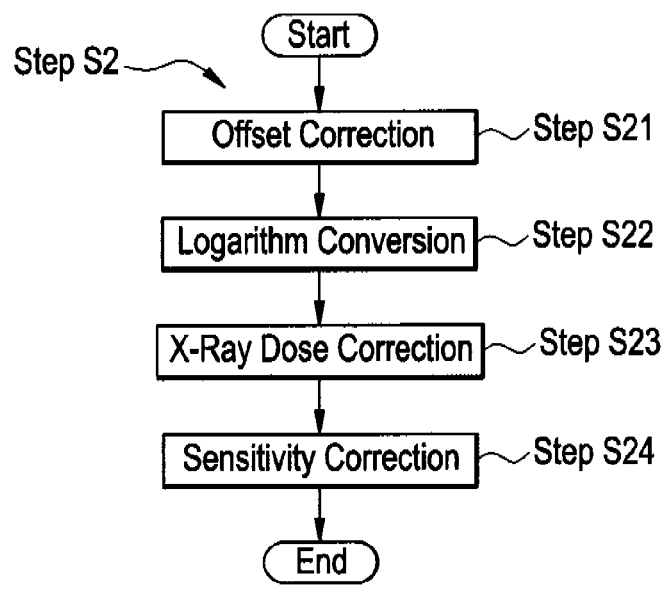

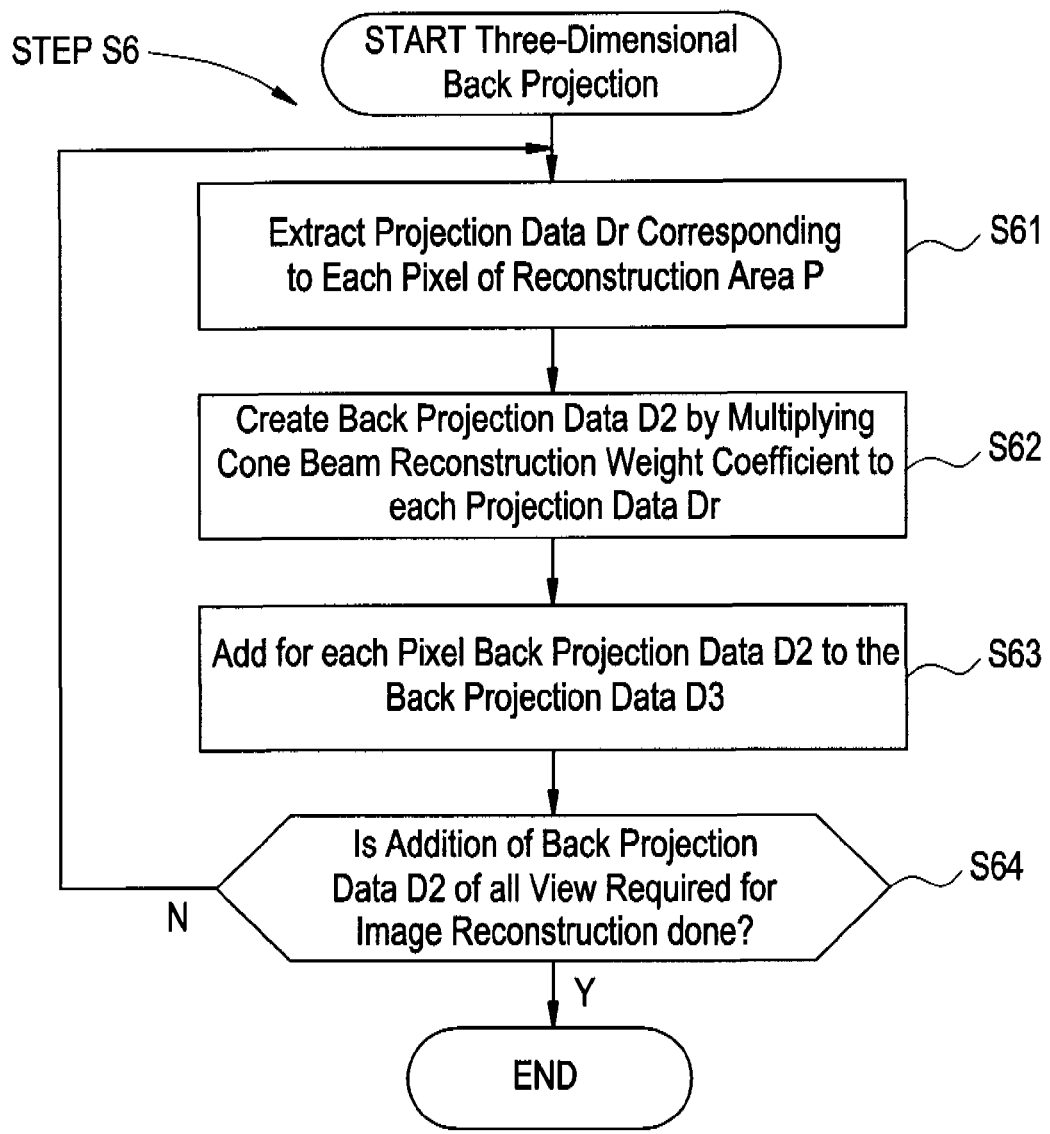

Reconstruction Area

P view=0°

Dr(0°,x,y)

Reconstruction Area

P view=0°

D2(0°,x,y)

CT Value Conversion in the Conventional Scan of the Prior Art

Flow of CT Value Adjustment

Deviation of CT Value and the Amount of Modification of Slope and Bias

Diference of Corresponding Detector Row in the Position of each Pixel of the Tomographic Image Difference of Corresponding Detector Row of the Pixel of Tomographic Image in each View Uniformity of Tomographic Image in z Direction in a Three-Dimensional Image z Direction Uniformity of Pixels in their Respective z Position is Required Example of Three-Dimensional MPR Display, Three-Dimensional Display Tomographic Image

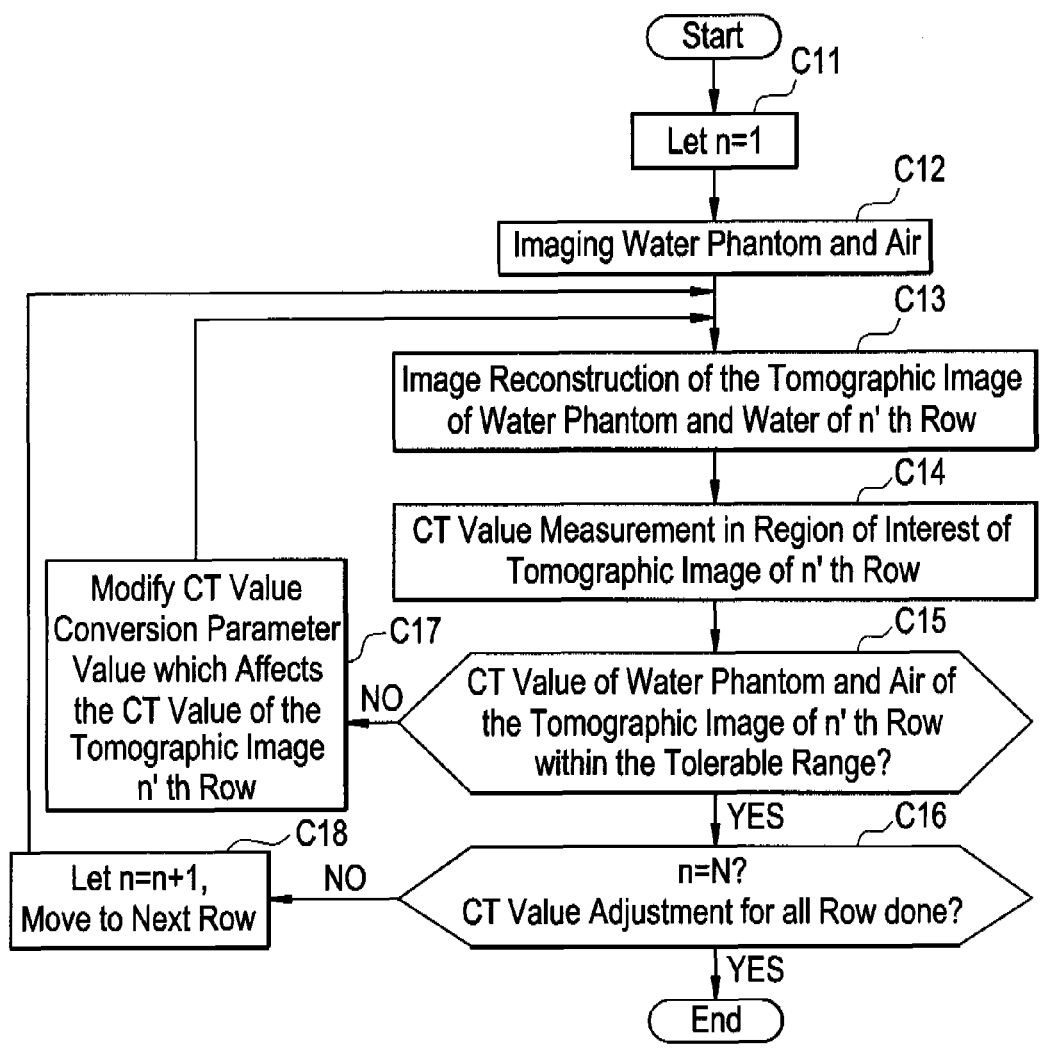

X-RAY CT IMAGING METHOD AND X-RAY CT APPARATUS

CROSS REFERENCE TO RELATED APPLICATIONS

This application claims the benefit of Japanese Application No. 2005-327266 filed Nov. 11, 2005.

BACKGROUND OF THE INVENTION

The present invention relates to an X-ray CT (computed tomography) apparatus having a multi column X-ray detector or a two-dimensional X-ray detector of matrix arrangement represented by a flat panel X-ray detector and X-ray CT imaging method, as well as to a CT value conversion of pixels in a tomographic image made by a conventional (axial) scan or cinescan or helical scan.

In the conventional technique a multi column X-ray detector type X-ray CT apparatus or an X-ray CT apparatus by a two-dimensional X-ray area detector of matrix arrangement represented by a flat panel, reconstructs a tomographic image Gj (x, y) of row j from the projection data of two-dimensional X-ray area detector of row j, and uses the CT value conversion parameters of the two-dimensional X-ray area detector of row j to perform a CT value conversion after a three-dimensional back-projection process in the three-dimensional image reconstruction as shown in FIG. 15 (c.f., JP-A-2004-073360). However, in the three-dimensional back projection process in the three-dimensional image reconstruction, because the image reconstruction of one single tomographic image uses the projection data derived from a plurality of rows of two-dimensional X-ray area detectors, the difference of characteristics of two-dimensional X-ray area detector in each row may pose a problem if only one row of CT value conversion parameters is used.

In a multi column X-ray detector type X-ray CT apparatus, or an X-ray CT apparatus having two-dimensional X-ray area detectors of matrix arrangement represented by a flat panel, the problem of exposure to unused X-ray tends to aggravate along with the increase of the cone angle of the X-ray cone beam.

SUMMARY OF THE INVENTION

The object of the present invention therefore is to provide in a conventional scan (axial scan) or cinescan or helical scan by an X-ray CT apparatus having a multi column X-ray detector or a two-dimensional area X-ray detector of matrix arrangement represented by a flat panel X-ray detector, an X-ray CT imaging method or an X-ray CT apparatus which performs appropriate CT value conversion even in a three-dimensional image reconstruction so as to achieve the uniformity of the tomographic image in z-axis.

In accordance with the present invention the dispersion in the data range of projection data of each row derived from the difference of the quality of the receiving X-ray is normalized to arrange and adjust the gain of the projection data such that each pixel in a tomographic image corresponds to a CT value to permit correct CT value conversion. Alternatively, by taking into account the contribution rate of the CT value adjustment parameters, which is different in each row of the two-dimensional X-ray area detector, to a position in a tomographic image or to the position of each pixel in a tomographic image, the present invention provides an X-ray CT imaging method and X-ray CT apparatus wherein the CT value adjustment parameters of each tomographic image or of each pixel of each tomographic image may be determined.

In a first aspect, the present invention provides an X-ray CT apparatus comprising: an X-ray data acquisition means for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction means for reconstructing an image from the projection data acquired by the X-ray data acquisition means; an image display means for displaying a tomographic image thus reconstructed; and an imaging condition setting means for setting various imaging conditions in an imaging of a tomographic image, wherein the X-ray CT apparatus comprises an image reconstruction means for performing data conversion of projection data before a three-dimensional back projection process to convert CT values of a tomographic image.

The X-ray CT apparatus in accordance with the first aspect described above, the range of projection data of each row after having convoluted reconstruction function may be normalized to arrange before the three-dimensional back projection process so that each pixel in a tomographic image reconstructed can be converted to an appropriate CT value.

In a second aspect, the present invention provides an X-ray CT apparatus comprising: an X-ray data acquisition means for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction means for reconstructing an image from the projection data acquired by the X-ray data acquisition means; an image display means for displaying a tomographic image thus reconstructed; and an imaging condition setting means for setting various imaging conditions in an imaging of a tomographic image, wherein the X-ray CT apparatus comprises an image reconstruction means for performing data conversion of the projection data prior to the convolution of the reconstruction function to perform the CT value conversion of a tomographic image.

In the X-ray CT apparatus in accordance with the second aspect described above, the range of projection data of each row after the preprocess prior to the convolution of reconstruction function, or after beam hardening correction, is normalized to arrange by CT value conversion so as to appropriately convert CT value of each pixel of a tomographic image reconstructed.

In a third aspect, the present invention provides an X-ray CT apparatus in accordance with the X-ray CT apparatus of the first or second aspect, wherein the X-ray CT apparatus comprises an image reconstruction means for image reconstruction by a CT value conversion parameter for each row of a two-dimensional X-ray area detector for the data conversion of projection data.

In the X-ray CT apparatus in accordance with the third aspect described above, since the difference of data range of projection data due to the dispersion or change of sensitivity in each row is adjusted by a CT value conversion parameter for each row of a multi column X-ray detector in the first or second aspect, each pixel in a tomographic image thus reconstructed can be converted to an appropriate CT value.

In a fourth aspect, the present invention provides an X-ray CT apparatus in accordance with the X-ray CT apparatus of the third aspect wherein the X-ray CT apparatus comprises an image reconstruction means for determining the CT value conversion parameters for each row of the two-dimensional X-ray area detector by taking into account the contribution rate to each pixel in a tomographic image.

In the X-ray CT apparatus in accordance with the fourth aspect described above, because the parameters for CT value conversion of each row in a multi column X-ray detector is determined by determining the contribution rate of each pixel of a tomographic image and of each row in the multi column X-ray detector so as for the CT value of the tomographic image reconstructed to be correctly adjusted in the third aspect of the present invention, each pixel in a tomographic image reconstructed can be converted to an appropriate CT value.

In a fifth aspect, the present invention provides an X-ray CT apparatus comprising: an X-ray data acquisition means for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction means for reconstructing an image from the projection data acquired by the X-ray data acquisition means; an image display means for displaying a tomographic image thus reconstructed; and an imaging condition setting means for setting various imaging conditions in an imaging of a tomographic image, wherein the X-ray CT apparatus comprises an image reconstruction means for performing CT value conversion of tomographic images by taking into account three-dimensional position of each pixel of a tomographic image and the position of data acquisition geometric system in the X-ray cone beam after three-dimensional back projection processing.

In the X-ray CT apparatus in accordance with the fifth aspect described above, since three-dimensional position of a tomographic image in the X-ray cone beam and the position of data acquisition geometric system are taken into account after the three-dimensional back projection processing, so that the contribution rate of each row of multi column X-ray detector into each pixel of a tomographic image is determined, CT value conversion of each pixel of a tomographic image can be performed by taking into account the dispersion of or fluctuation of each row of a multi column X-ray detector.

In a sixth aspect, the present invention provides an X-ray CT apparatus comprising: an X-ray data acquisition means for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction means for reconstructing an image from the projection data acquired by the X-ray data acquisition means; an image display means for displaying a tomographic image thus reconstructed; and an imaging condition setting means for setting various imaging conditions in an imaging of a tomographic image, wherein the X-ray CT apparatus comprises an image reconstruction means for performing CT value conversion of tomographic images by taking into account the contribution rate of each row of a two-dimensional X-ray area detector into each pixel of a tomographic image after the three-dimensional back projection processing.

In the X-ray CT apparatus in accordance with the sixth aspect described above, since the amount of the contribution of each row of the X-ray two-dimensional area detector to each pixel of a tomographic image after the three-dimensional back projection processing is previously taken into account, a CT value conversion table from the CT value conversion parameters of each row of a multi column X-ray detector into each pixel of a tomographic image can be determined.

In a seventh aspect, the present invention provides an X-ray CT apparatus in accordance with one of fifth or sixth aspect described above, wherein the X-ray CT apparatus comprises an image reconstruction means for determining the contribution rate from each row to each pixel of a tomographic image based on the position of X-ray focus, the position of each row of the two-dimensional X-ray area detector, the position on an x-y plane of each pixel of the tomographic image, and the z-axis coordinate position on the tomographic image, and for determining the CT value conversion parameters of each row of multi column X-ray detector based on the contribution rate thus determined, where the revolving plane of the data acquisition system is defined as x-y plane, and the moving direction of the imaging table which is normal thereto is defined as z direction.

In the X-ray CT apparatus in accordance with the seventh aspect described above, since the contribution rate from the x,y coordinates of each pixel of a tomographic image or the z-axis coordinate position of the tomographic image to each row of the multi column X-ray detector is determined, in accordance with the fifth or sixth aspect described above, the CT value conversion table after the three-dimensional back projection processing can be determined from the CT value conversion parameters of each detector row.

In a eighth aspect, the present invention provides an X-ray CT apparatus in accordance with the seventh aspect, wherein the X-ray CT apparatus comprises an image reconstruction means for determining CT value conversion parameters from the z-axis coordinate position on a tomographic image, where the revolving plane of the data acquisition system is defined as x-y plane, and the moving direction of the imaging table which is perpendicular thereto is defined as z direction.

In the X-ray CT apparatus in accordance with the eighth aspect described above, since the contribution rate to each row of multi column X-ray detector from the x, y coordinate of each row of a tomographic image or the z coordinate position of the tomographic image is determined in the seventh aspect described above, the CT value conversion table after the three-dimensional back projection processing can be determined from the CT value conversion parameters of each detector row.

In a ninth aspect, the present invention provides an X-ray CT apparatus in accordance with any one of the fifth to eighth aspect described above, wherein the X-ray CT apparatus comprises an image reconstruction means for determining, in particular in a helical scan, the CT value conversion parameters in correspondence with the helical pitch and the z-axis coordinate position of the tomographic image.

In the X-ray CT apparatus in accordance with the ninth aspect described above, in the fifth to eighth aspect described above, CT value conversion parameters can be determined in correspondence with the z-axis coordinate position if the computation is given based on the CT value conversion parameter of each row of the multi column X-ray detector from the helical pitch and the z-axis coordinate position of the tomographic image.

In a tenth aspect, the present invention provides an X-ray CT apparatus in accordance with any one of first to ninth aspect described above, wherein the X-ray CT apparatus comprises an image reconstruction means which is capable of continuously specifying the z-axis coordinate position in the z-axis direction of the tomographic image.

In the X-ray CT apparatus in accordance with the tenth aspect described above, in accordance with first to ninth aspect described above, the z-axis coordinate position of the tomographic image is defined, so, the CT value conversion parameters can be determined continuously in the z-axis coordinate position of the tomographic image.

In an eleventh aspect, the present invention provides an X-ray CT imaging method comprising the steps of: X-ray data acquisition step for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction step for reconstructing an image from the projection data acquired by the X-ray data acquisition step; an image display step for displaying a tomographic image thus reconstructed; and an imaging condition setting step for setting various imaging conditions in an imaging of a tomographic image, wherein the X-ray CT imaging method comprises the step of performing data conversion of projection data prior to the three-dimensional back projection processing and performing CT value conversion of a tomographic image.

In the X-ray CT imaging method in accordance with the eleventh aspect described above, since the range of projection data of each row after the convolution of reconstruction function before the three-dimensional back projection processing is normalized to arrange, each pixel thus reconstructed can be converted to an appropriate CT value.

In a twelfth aspect, the present invention provides an X-ray CT imaging method comprising the steps of: X-ray data acquisition step for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction step for reconstructing an image from the projection data acquired by the X-ray data acquisition step; an image display step for displaying a tomographic image thus reconstructed; and an imaging condition setting step for setting various imaging conditions in an imaging of a tomographic image, wherein the X-ray CT imaging method comprises an image reconstruction step of performing the data conversion of the projection data prior to the convolution of reconstruction function and of performing the CT value conversion of the tomographic image.

In the X-ray CT imaging method in accordance with the twelfth aspect described above, since the range of the projection data of each row before preprocessing or after the beam hardening correction prior to the convolution of the reconstruction function is normalized to arrange, each pixel of the tomographic image thus reconstructed can be converted to an appropriate CT value.

In a thirteenth aspect the present invention provides an X-ray CT imaging method in accordance with the X-ray CT imaging method of the eleventh or twelfth aspect described above, wherein the X-ray CT imaging method comprises the step of image reconstruction for performing the image reconstruction by using the CT value conversion parameter for each row of the two-dimensional X-ray area detector for the data conversion of the projection data.

In the X-ray CT imaging method in accordance with the thirteenth aspect described above, in accordance with the eleventh or twelfth aspect described above, since the difference of data range of the projection data due to the dispersion or fluctuation of the sensitivity of each row is adjusted with the CT value conversion parameters for each row of the multi column X-ray detector in accordance with the eleventh or twelfth aspect described above, each pixel of the tomographic image thus reconstructed can be converted to an appropriate CT value.

In a fourteenth aspect, the present invention provides an X-ray CT imaging method in accordance with the thirteenth aspect, wherein the X-ray CT imaging method comprises the step of image reconstruction for determining the CT value conversion parameter for each row of the two-dimensional X-ray area detector by taking into account the contribution rate to each pixel of the tomographic image.

In the X-ray CT imaging method in accordance with the fourteenth aspect described above, in the thirteenth aspect described above, since the CT value conversion parameter of each row of the multi column X-ray detector is determined by determining the contribution rate of each pixel of the tomographic image and each row of the multi column X-ray detector so as to correctly adjust the CT value of the tomographic image thus reconstructed, each pixel of the tomographic image thus reconstructed can be converted to an appropriate CT value.

In a fifteenth aspect, the present invention provides an X-ray CT imaging method comprising the steps of: X-ray data acquisition step for acquiring X-ray projection data by revolving an X-ray generator and a two-dimensional X-ray area detector of the type of multi column X-ray detector or of matrix arrangement represented by a flat panel X-ray detector, for detecting X-ray in opposition, around a rotation center therebetween, and by transmitting through an object placed therebetween; an image reconstruction step for reconstructing an image from the projection data acquired by the X-ray data acquisition step; an image display step for displaying a tomographic image thus reconstructed; and an imaging condition setting step for setting various imaging conditions in an imaging of a tomographic image, wherein the X-ray CT imaging method comprises the step of image reconstruction for performing the CT value conversion by taking into account the three-dimensional position of each pixel of the tomographic image in the X-ray cone beam and the position of the data acquisition geometric system after the three-dimensional back projection processing.

In the X-ray CT imaging method in accordance with the fifteenth aspect described above, since the three-dimensional position of the tomographic image in the X-ray cone beam and the position of the data acquisition geometric system after the three-dimensional back projection processing are taken into account, and the contribution rate of each row of the multi column X-ray detector to each pixel of the tomographic image is determined, the CT value conversion of each pixel of the tomographic image can be performed by taking into account the dispersion or fluctuation of each row of the multi column X-ray detector.

In a sixteenth aspect the present invention provides an X-ray CT imaging method comprising the steps of: X-ray data acquisition step for acquiring X-ray projection data by revolving an X-ray generator and a two-dimensional X-ray area detector of the type of multi column X-ray detector or of matrix arrangement represented by a flat panel X-ray detector for detecting X-ray in opposition, around a rotation center therebetween, and by transmitting through an object placed therebetween; an image reconstruction step for reconstructing an image from the projection data acquired by the X-ray data acquisition step; an image display step for displaying a tomographic image thus reconstructed; and an imaging condition setting step for setting various imaging conditions in an imaging of a tomographic image, wherein the X-ray CT imaging method comprises the step of image reconstruction for performing the CT value conversion of the tomographic image by taking into account the contribution rate of each row of the two-dimensional X-ray area detector to each pixel of the tomographic image after the three-dimensional back projection processing.

In the X-ray CT imaging method in accordance with the sixteenth aspect described above, since the contribution of each row of the X-ray two-dimensional area detector to each pixel of the tomographic image is previously taken into account after the three-dimensional back projection processing, CT value conversion table to each pixel of the tomographic image can be determined from the CT value conversion parameters of each row of the multi column X-ray detector.

In the seventeenth aspect, the present invention provides an X-ray CT imaging method in accordance with the fifteenth or sixteenth aspect described above, wherein the X-ray CT imaging method comprises an image reconstruction step for determining the contribution rate of each row to each pixel of the tomographic image from the position of X-ray focus, the position of each row of two-dimensional X-ray area detector, the position on the x-y plane of each pixel of the tomographic image, and the z-axis coordinate position on the tomographic image, then determining the CT value conversion parameters of each row of multi column X-ray detector based on the contribution rate, where the revolving plane of the data acquisition system is defined as x-y plane, and the moving direction of the imaging table which is perpendicular thereto is defined as z direction.

In the X-ray imaging method in accordance with the seventeenth aspect described above, in the fifteenth or sixteenth aspect, since the contribution rate to each row of the multi column X-ray detector is determined from the x,y coordinate of each pixel of the tomographic image or the z-axis coordinate position of the tomographic image, CT value conversion table after the three-dimensional back projection processing can be determined from the CT value conversion parameters of each detector row.

In an eighteenth aspect, the present invention provides an X-ray CT imaging method in accordance with the seventeenth aspect, wherein the X-ray CT imaging method comprises the step of image reconstruction for determining CT value conversion parameters from the z-axis coordinate position on the tomographic image, where the revolving plane of the data acquisition system is defined as x-y plane, and the moving direction of the imaging table which is perpendicular thereto is defined as z direction.

In the X-ray imaging method in accordance with the eighteenth aspect described above, in the seventeenth aspect since the contribution rate to each row of multi column X-ray detector from the x, y coordinate of each pixel of the tomographic image or the z-axis coordinate position of the tomographic image, the CT value conversion table after the three-dimensional back projection processing can be determined from the CT value conversion parameters of each detector row.

In a nineteenth aspect, the present invention provides an X-ray CT imaging method in accordance with any one of the fifteenth to eighteenth aspect described above, wherein the X-ray CT imaging method comprises the step of image reconstruction for determining in particular in the helical scan CT value conversion parameter in correspondence with the helical pitch and the z-axis coordinate position of the tomographic image.

In the X-ray imaging method in accordance with the nineteenth aspect described above, in the fifteenth to eighteenth aspect described above, since the CT value conversion parameters of each row of the multi column X-ray detector is calculated from the helical pitch and the z-axis coordinate position of the tomographic image, the CT value conversion parameter in correspondence with the z-axis coordinate position can be determined.

In a twentieth aspect, the present invention provides an X-ray CT imaging method in accordance with any one of the eleventh to nineteenth aspect, wherein the X-ray CT imaging method comprises the step of image reconstruction for continuously specifying the z-axis coordinate position of the tomographic image in the z direction.

In the X-ray imaging method in accordance with the twentieth aspect described above, in the eleventh to nineteenth aspect described above, when the z-axis coordinate position of the tomographic image is determined CT value conversion parameters may be continuously determined on the z-axis coordinate position of the tomographic image.

EFFECT OF THE INVENTION

In accordance with the X-ray CT apparatus or the X-ray CT imaging method of the present invention, an X-ray CT imaging method or an X-ray CT apparatus can be achieved which performs appropriately the CT value conversion and provides the uniformity of the tomographic image in the z direction, in a conventional scan (axial scan) or cinescan or helical scan by an X-ray CT apparatus having a multi column X-ray detector or a two-dimensional area X-ray detector of matrix arrangement represented by a flat panel X-ray detector.

BRIEF DESCRIPTION OF THE DRAWINGS

FIG. 5 is a schematic flow diagram illustrating the overview of the operation of the X-ray CT apparatus in accordance with the preferred embodiment of the present invention;

FIG. 6 is a schematic flow diagram illustrating the details of preprocessing;

FIG. 7 is a schematic flow diagram illustrating the details of three-dimensional image reconstruction processing;

FIG. 23 is a schematic flow diagram of CT value adjustment in case of three-dimensional image reconstruction.

DETAILED DESCRIPTION OF THE INVENTION

The present invention will be described in greater details with reference to a preferred embodiment shown in the accompanying drawings. It should be noted that the preferred embodiments disclosed herein are not to be considered to limit the invention.

Figure 1:
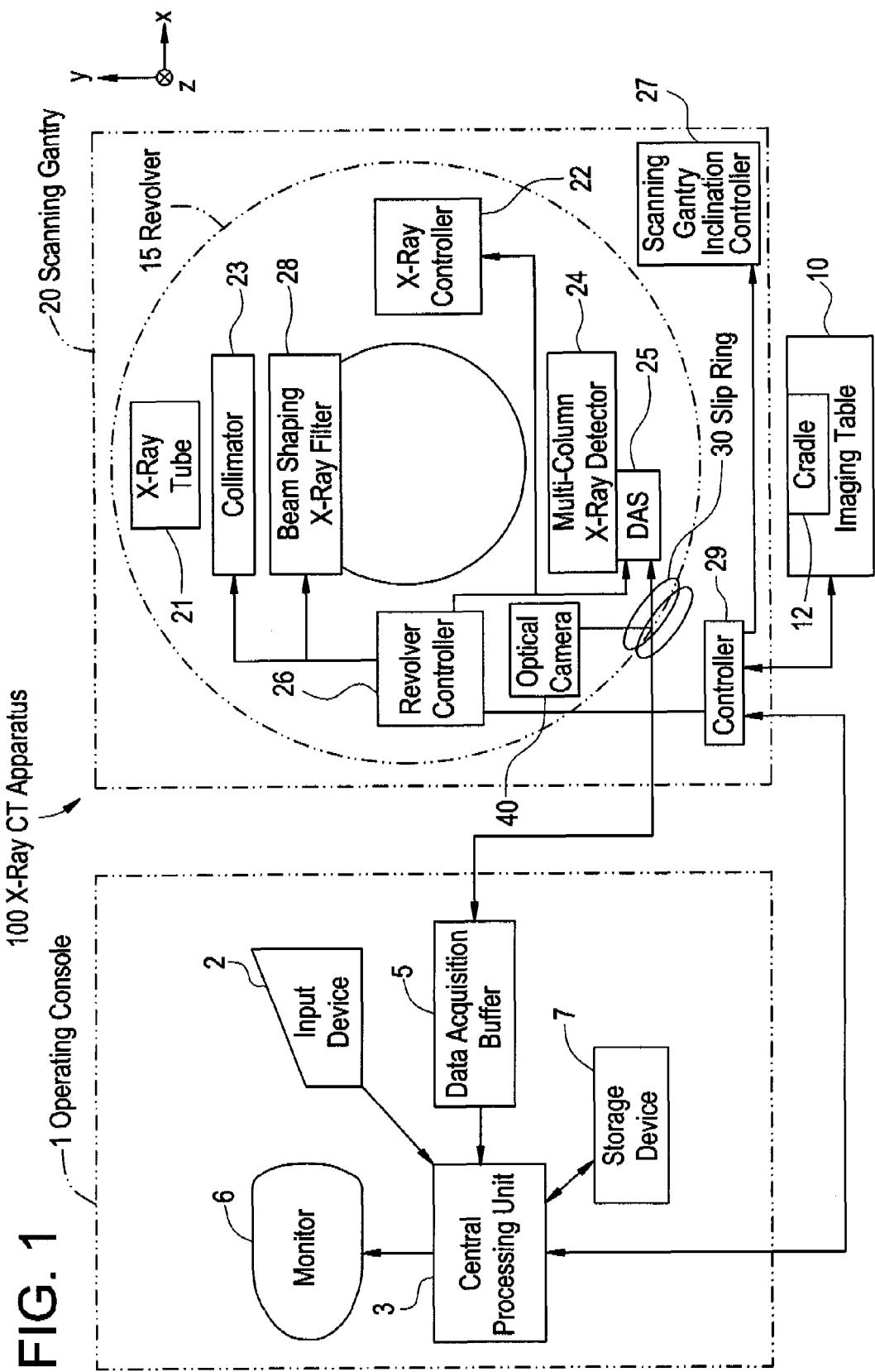
FIG. 1 is a schematic block diagram illustrating an X-ray CT apparatus in accordance with the preferred embodiment of the present invention.

Referring to FIG. 1, there is shown a schematic block diagram of an X-ray CT apparatus in accordance with a preferred embodiment of the present invention. The X-ray CT apparatus 100 includes an operating console 1, an imaging table 10, and a scanning gauntry 20.

The operating console 1 incorporates an input device 2 for receiving the input from the operator, a central processing unit 3 for executing the preprocessing, image reconstruction processing, and postprocessing, a data acquisition buffer 5 for acquiring the X-ray detector data acquired by the scanning gauntry 20, a monitor 6 for displaying a tomographic image reconstructed from the projection data determined by preprocessing the X-ray detector data, and a storage device 7 for storing programs, X-ray detector data, projection data, and X-ray tomographic images.

Figure 14:
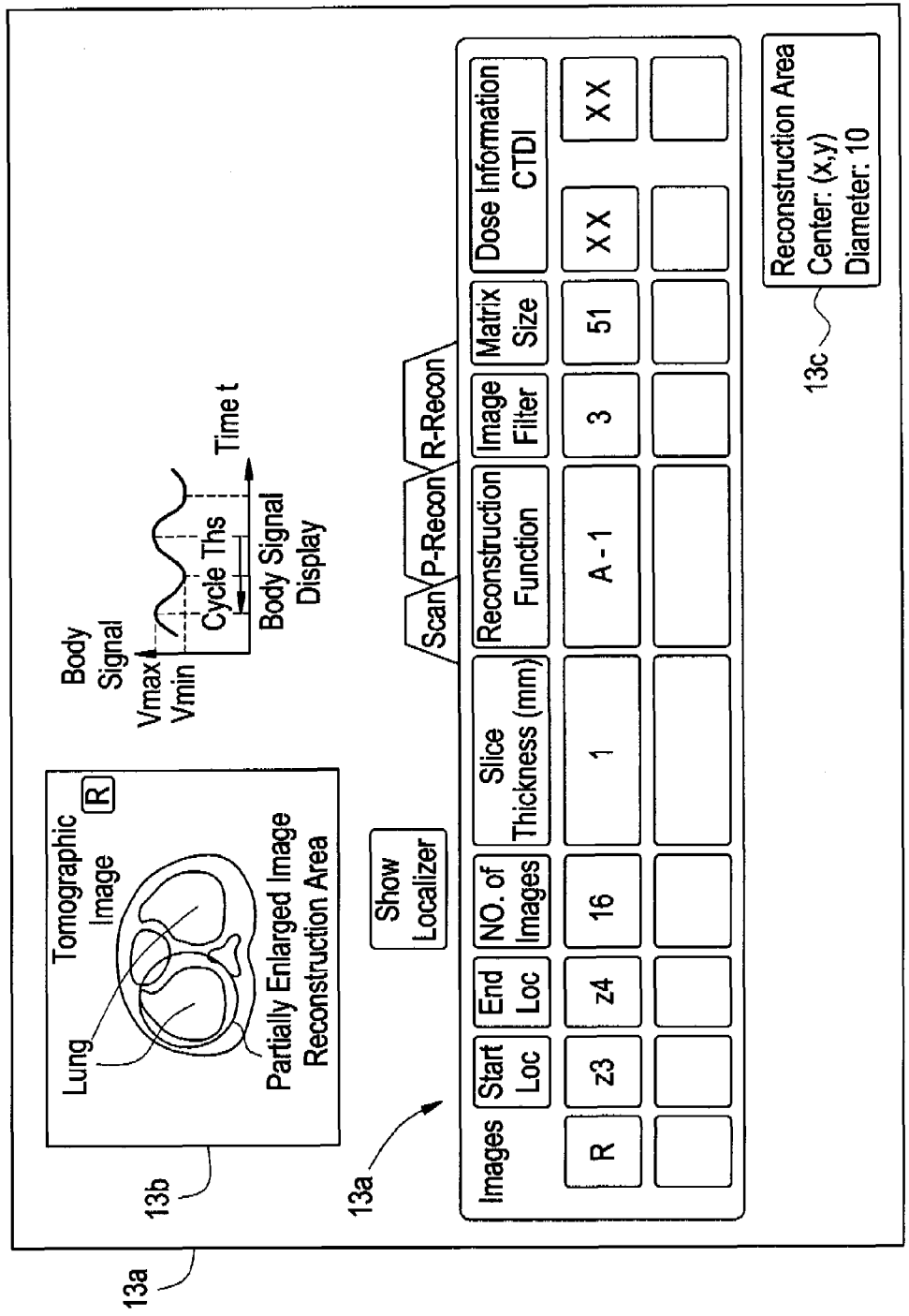
FIG. 14 is a schematic diagram illustrating the imaging condition input display screen of the X-ray CT apparatus.
Figure 15:
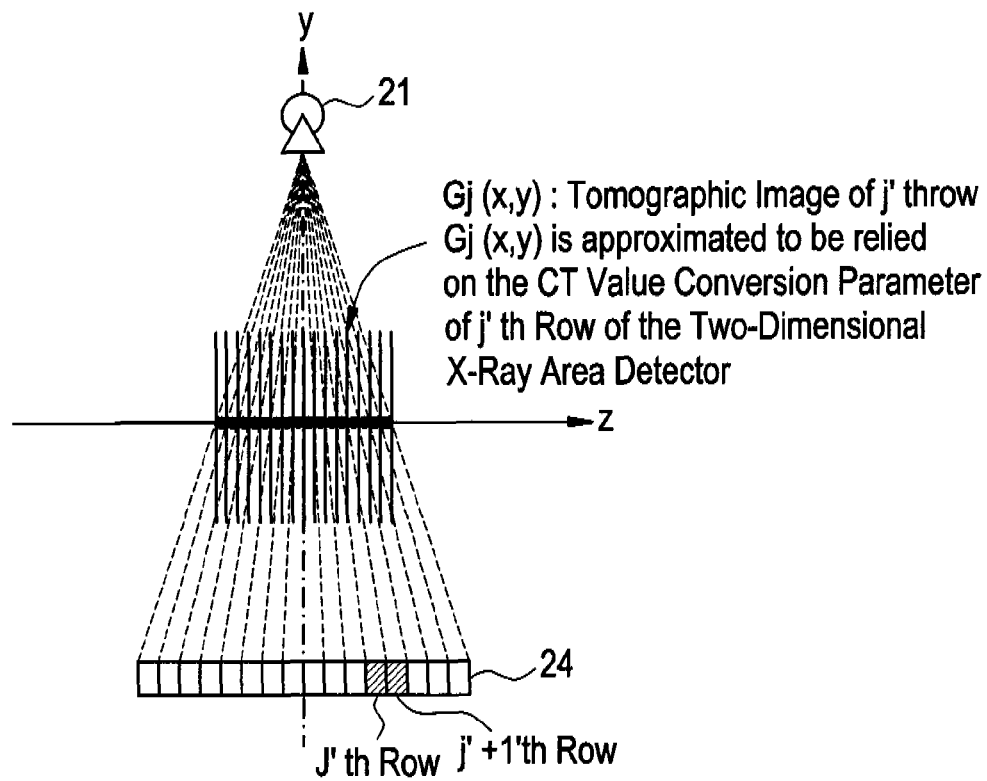
FIG. 15 is a schematic diagram illustrating the CT value conversion in the conventional scan of the Prior Art.

The input of imaging condition is input from the input device 2 and stored in the storage device 7. FIG. 14 shows an example of the imaging condition input display screen.

The imaging table 10 includes a cradle 12 for carrying in and out of the opening of the scanning gauntry 20 with an object being mounted thereon. The cradle 12 is elevated up and down by the motor incorporated within the imaging table 10 and the table is linearly translated thereby.

The scanning gauntry 20 includes an X-ray tube 21, an X-ray controller 22, a collimator 23, a beam shaping X-ray filter 28, a multi column X-ray detector 24, DAS (data acquisition system) 25, a revolver controller 26 for controlling the X-ray tube 21 and the like revolving around the body axis of the object, a controller 29 for communicating the control signals with the operating console 1 and the imaging table 10. The beam shaping X-ray filter 28 is an X-ray filter, the thickness of which is most thinner in the direction of X-ray directing toward the imaging center or the revolving center, and is gradually thickening toward the periphery, so as to more absorb the X-ray in the periphery. This type of filter allows the body surface of the object having a cross-sectional shape of circle or oval to be less exposed to the X-ray. A scanning gauntry inclination controller 27 allows the gauntry 20 to incline +/−30 degrees forward and backward in z-axis.

The X-ray tube 21 and the multi column X-ray detector 24 revolves around the revolving center IC. When y direction is defined as the vertical direction, x direction is defined as horizontal direction, and the z direction is defined as the direction perpendicular to both and along with the moving direction of the table and cradle, the revolving plane of the X-ray tube 21 and the multi column X-ray detector 24 is defined as x-y plane. the moving direction of the cradle 12 is in z direction.

Figure 2:
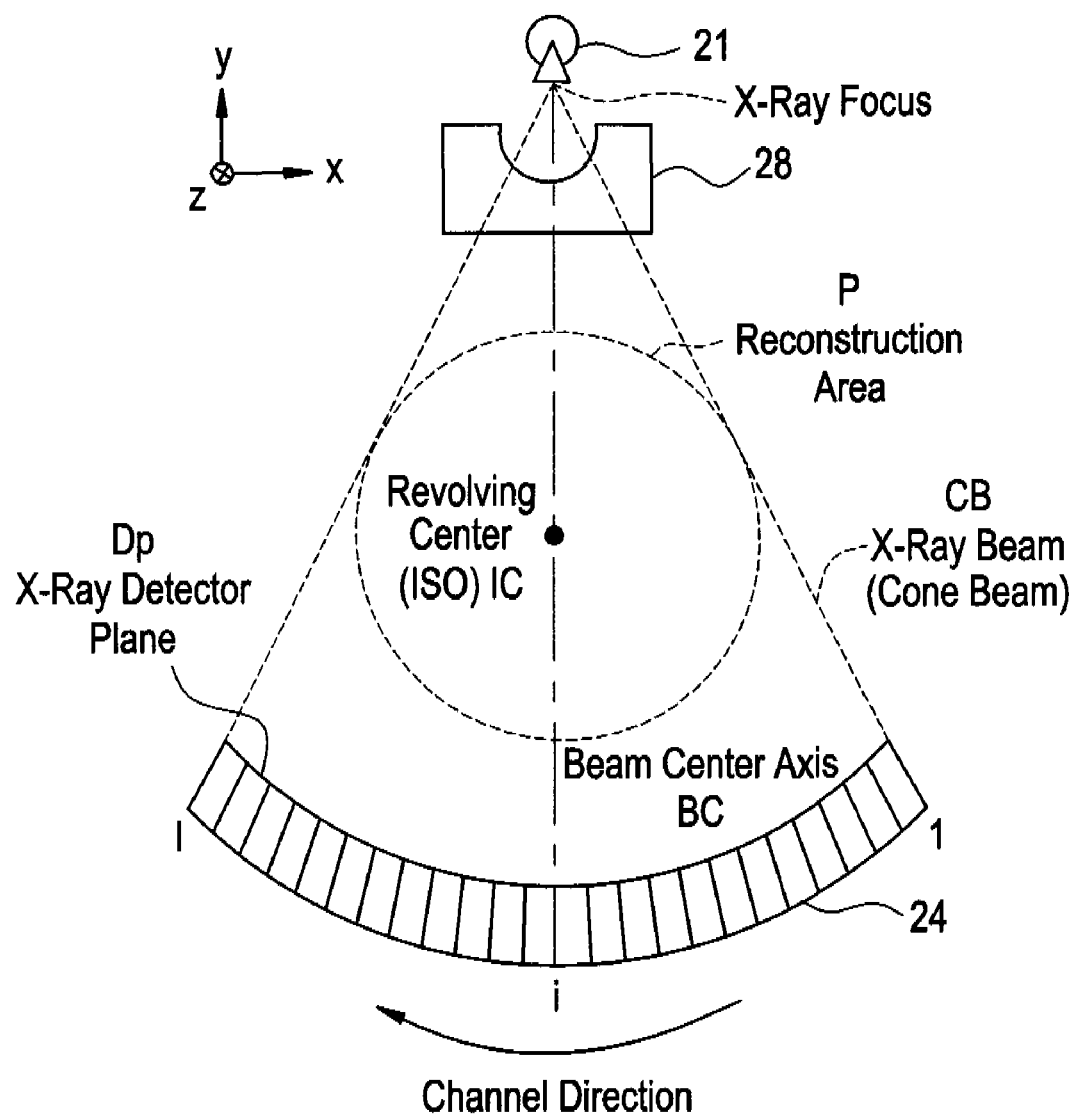
FIG. 2 is a schematic diagram of an X-ray generator (X-ray tube) and multi column X-ray detector taken along in the x-y plane.
Figure 3:
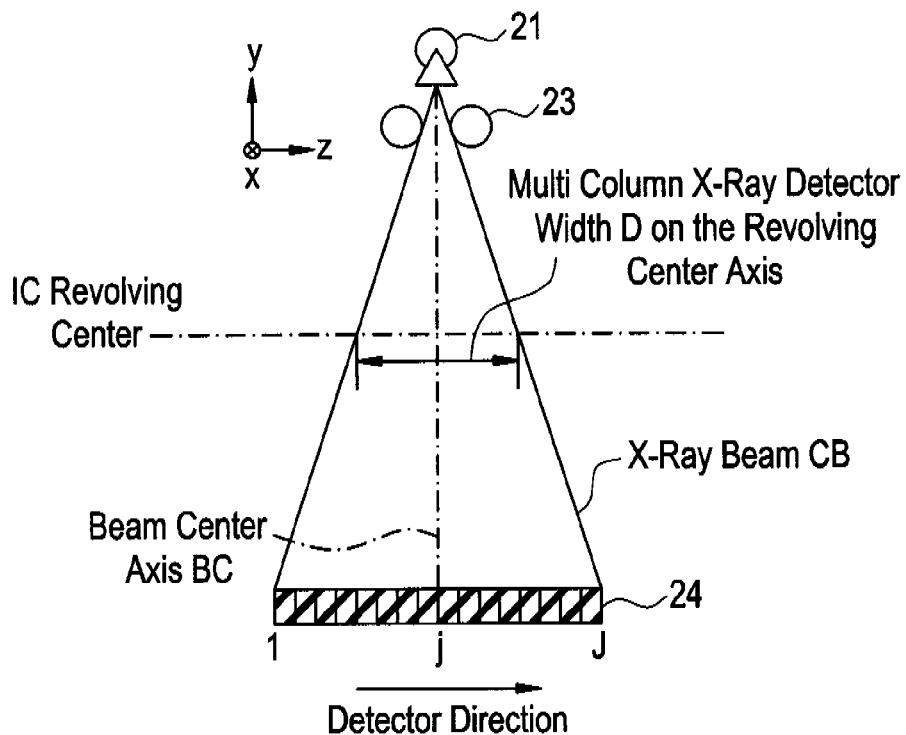
FIG. 3 is a schematic diagram of an X-ray generator (X-ray tube) and multi column X-ray detector taken along in the y-z plane.

FIG. 2 and FIG. 3 are schematic diagrams of the geometric arrangement of the X-ray tube 21 and the multi column X-ray detector 24 in the x-y plane or y-z plane.

The X-ray tube 21 generates an X-ray beam referred to as the cone beam CB. The view angle is 0 degree when the central axis of the cone beam CB is in parallel to the y direction.

The multi column X-ray detector 24 includes a X-ray detector array of for example 256 row in the z direction. Each X-ray detector row includes X-ray detector channels of for example 1024 channels in the channel direction.

In FIG. 2, the X-ray beam emitted from the X-ray focal point of the X-ray tube 21 is shaped by the beam shaping X-ray filter 28 to control spatially the amount of X-ray such that more X-ray is irradiated around the center of the reconstruction area P and less X-ray is irradiated in the periphery of the reconstruction area P, then the X-ray is absorbed by the object placed within the reconstruction area P, the X-ray transmitted through the object will be acquired by the multi column X-ray detector 24 as the X-ray detector data.

In FIG. 3, the X-ray beam emitted from the X-ray focal point of the X-ray tube 21 is controlled in the slice thickness direction by the collimator 23, in other words controlled such that the X-ray beam width becomes D in the revolving center IC, then the X-ray is absorbed by the object placed around the revolving center IC, the X-ray transmitted therethrough is acquired by the multi column X-ray detector 24 as the X-ray detector data.

The projection data of X-ray emitted and acquired will be A/D converted by the multi column X-ray detector 24 to DAS 25, and will be input to a data acquisition buffer data acquisition buffer 5 through a slip ring 30. The data input into the data acquisition buffer 5 will be processed by a program of the storage device 7 in the central processing unit 3 to display on the monitor 6 after image is reconstructed as a tomographic image.

Figure 4:
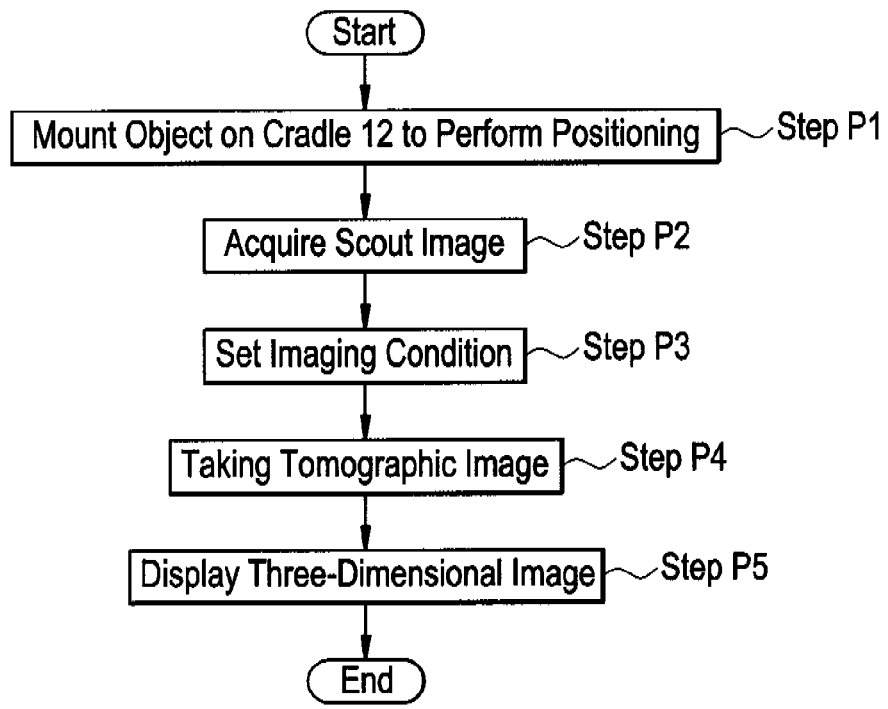
FIG. 4 is a schematic flow diagram illustrating the flow of object imaging.

FIG. 4 shows a flow diagram illustrating the overview of the operation of the X-ray CT apparatus in accordance with the preferred embodiment.

In step P1, an object is mounted on the cradle 12, the position is registered. The object placed on the cradle 12 will have the reference points of each part registered with the slice light center position of the scanning gauntry 20.

In step P2, a scout image is acquired. The scout image will be imaged at 0 degree and 90 degrees in normal condition, however it may be 90 degrees scout image only according to the body part such as the head. The imaging of a scout image will be described in greater details later herein.

In step P3 the imaging condition will be set. In the ordinary imaging condition the image will be taken while displaying on the scout image the size and position of the tomographic image to be imaged. In this case the information about the amount of X-ray will be displayed as the amount of entire one revolution of the helical scan or variable pitch helical scan or conventional scan (axial scan) or cinescan. In the cinescan when the number of rotation or rotation time is input the information about the amount of X-ray for the time or revolution input at the area of the interest.

In step P4 a tomographic image is taken. The imaging of a tomographic image will be described in greater details later.

Figure 21:
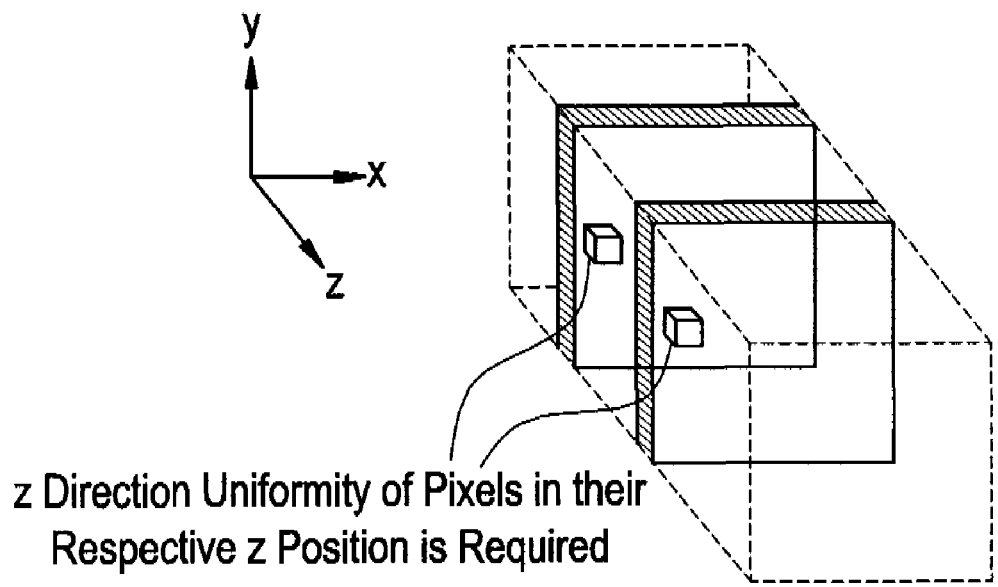
FIG. 21 is a schematic diagram illustrating the uniformity of the tomographic image in the z direction in a three-dimensional image.
Figure 22:
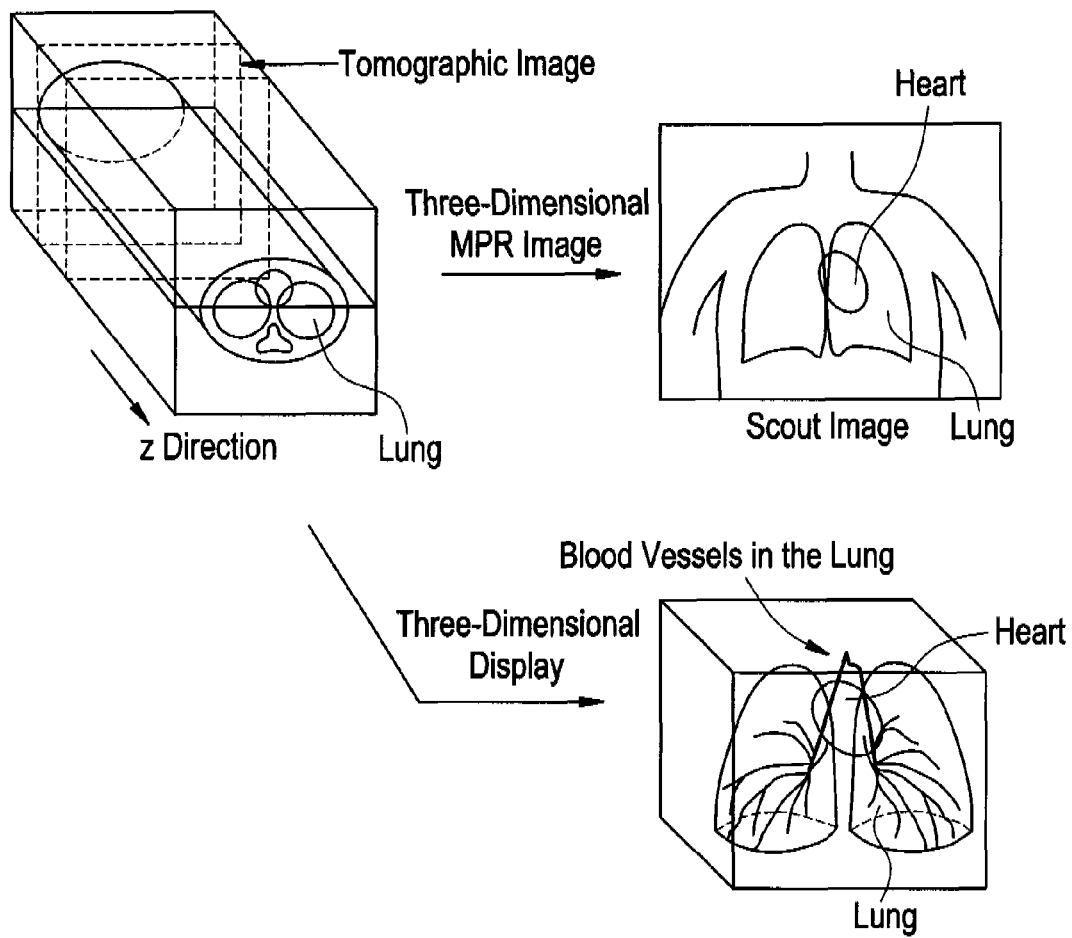
FIG. 22 is a schematic diagram illustrating an example of three-dimensional MPR display and three-dimensional display.

In step P5 a three-dimensional image display will be performed. In general the displaying method called as three-dimensional image display include a three-dimensional display (volume rendering), MPR multi plain reformat) display, MIP (maximum intensity projection) display, and so on. In particular when a two-dimensional X-ray area detector of matrix arrangement such as represented by a multi column X-ray detector or a flat panel X-ray detector is used, the spatial resolution in the x-y plane of the tomographic image plane and in the z-direction of the moving direction of the cradle 12 are almost equal, and the isotropy of the pixel has been achieved, the importance of the three-dimensional image display is weighed on the diagnosis. In such a case the uniformity of the image quality in the z direction as shown in FIG. 21, more specifically the uniformity of the CT values is indispensable. FIG. 22 shows an example of three-dimensional MPR and three-dimensional display.

FIG. 5 shows a flow diagram illustrating the overview of the imaging operation of the tomographic image and the scout image in accordance with the X-ray CT apparatus 100 of the present invention.

In step S1, when using the helical scan, the X-ray tube 21 and the multi column X-ray detector 24 are revolved around the object, while the cradle 12 on the imaging table 10 is translated along with the table, the data acquisition operation is performed for the X-ray detector data. The X-ray detector data D0 (view, j, i) represented by the view angle 'view', detector row number 'j', and the channel number 'i' with the table translational movement z direction position Z table (view) will be acquired as X-ray detector data. In the variable pitch helical scan, assuming that not only the data acquisition in the range of constant velocity in helical scan mode, but also the data during the acceleration and deceleration will be acquired as data.

In the conventional scan (axial scan) or cinescan, the cradle 12 on the imaging table 10 is placed immobile in the z direction, the data acquisition system will be rotated once or plural times to acquire the data. When required, the data acquisition system will be moved to the next position in the z direction and revolved once or plural times to acquire the data of X-ray detector.

In the imaging of scout image, data acquisition operation is performed when the X-ray tube 21 and the multi column X-ray detector 24 are fixed while the cradle 12 on the imaging table 10 is translationally moved.

In step S2 the X-ray detector data D0 (view, j, i) is preprocessed to convert to the projection data. The preprocessing is comprised of, as shown in FIG. 6, step S21 offset correction, step S22 logarithm conversion, step S23 X-ray dose correction, and step S24 sensitivity correction.

In the imaging of scout image, the image is done when the preprocessed X-ray detector data is displayed with the pixel size in the channel direction and the pixel size in the z direction that is the cradle translational moving direction being matched to the display pixel size of the monitor 6.

In step S3, a beam hardening correction is performed on the preprocessed projection data D1 (view, j, i). In the beam hardening correction S3, assuming that the projection data having undergone the sensitivity correction S24 in the preprocessing S2 is D1 (view, j, i), and the data after the beam hardening correction S3 is D11 (view, j, i), then the beam hardening correction S3 can be given as in a form of polynomial as in the following equation 1.

[equation 1]

$$D11(\text{view}, j, i) = D1(\text{view}, j, i) \cdot (B0(j, i) + B1(j, i) \cdot D1(\text{view}, j, i) + B2(j, i) \cdot D1(\text{view}, j, i)2) \quad \text{(equation 1)}$$

At this time since the beam hardening correction can be done independently for each j row of the detector, if the tube voltage of each of data acquisition system is differently set in the imaging condition, the X-ray energy characteristics for each row of the detector can be corrected.

In step S4 a z filter convolution is performed for filtering in the z direction (row direction) the projection data D11 (view, j, i) with beam hardening.

More specifically, after preprocessing in each view angle in each data acquisition system, a filter having the row direction filter size of 5 rows as shown in equation 2 and equation 3 below is applied in the row direction to the projection data of the multi column X-ray detector D11 (view, j, i), (i=1 to CH, j=1 to ROW), having beam hardening correction applied.

[equation 2]

$$(w1(i), w2(i), w3(i), w4(i), w5(i)), \quad \text{(equation 2)}$$

$$\text{where } \sum_{K=1}^{5} W_k(i) = 1 \quad \text{(equation 3)}$$

The corrected detector data D12 (view, j, i) will be given as equation 4 below.

[equation 3]

$$D12(\text{view}, j, i) = \sum_{K=1}^{5} D11(\text{view}, j + k - 3, i) \cdot w_k(j)) \quad \text{(equation 4)}$$

When defining the maximum number of channels as CH, the maximum number of rows as ROW, then the equation 5 and equation 6 below can be given.

[equation 4]

$$D11(\text{view}, -1, i) = D11(\text{view}, 0, i) = D11(\text{view}, 1, i) \quad \text{(equation 5)}$$

$$D11(\text{view}, \text{ROW}, i) = D11(\text{view}, \text{ROW}+1, i) = D11(\text{view}, \text{ROW}+2, i) \quad \text{(equation 6)}$$

When changing the row direction filter coefficient for each channel, the slice thickness can be controlled in accordance with the distance from the image reconstruction center. Because in general in the tomographic image, the periphery has a thicker slice than the reconstruction center, when the row direction filter coefficient is varied in the center and in the periphery to largely change the row filter coefficient such that the width of the row direction filter coefficient in the vicinity of center channels may become wider, and the width of the row direction filter coefficient in the vicinity of peripheral channels may become narrower, the slice thickness can be uniform in the peripheral as well as the image reconstruction center.

As can be seen from the foregoing, by controlling the row direction filter coefficient in the center channels as well as the peripheral channels of the multi column X-ray detector 24, the slice thickness in the center and periphery can be adjusted. If the slice thickness is somewhat thicker by the row direction filter, the significant improvement of artifact and noise can be achieved. The degree of artifact improvement and the noise improvement can be controlled in this manner. In other words, the image quality in the tomographic image having three-dimensional image reconstructed or the x-y plane can be controlled. As another example, by using a deconvolution filer for the row direction (z direction) filter coefficient, a tomographic image having thinner slice thickness can also be achieved.

When required, the X-ray projection data of the fan beam may be converted to the X-ray projection data of the parallel beam.

In step S5, the reconstruction function is convoluted. More specifically, the data is applied with a Fourier transform, then multiplied with the reconstruction function, and applied with an invert Fourier transform. In the reconstruction function convolution S5, assuming that the data having z filter convolution is D12, the data having the reconstruction function convolution is D13, the reconstruction function to be convoluted is Kernel (j), then the reconstruction function convolution processing can be given as the equation 7 below.

[equation 5]

$$D13\,(\text{view},j,i)=D12\,(\text{view},j,i)*\text{Kernel}\,(j) \quad \text{(equation 7)}$$

The reconstruction function Kernel (j) may perform the reconstruction function convolution processing independently on each j row of the detector, so that the difference of the noise characteristics and the resolution characteristics in each row can be corrected.

In step S6, a three-dimensional back projection processing is done on the projection data D13 (view, j, i) having the reconstruction function convolution applied to determine the back projection data D3 (x, y, z). The image to be reconstructed is three-dimensional image reconstructed along with the x-y plane, which is normal to the z-axis. The reconstruction area P is assumed to be in parallel to the x-y plane in the following description. The three-dimensional back projection processing will be described in greater details with reference to FIG. 5 later.

In step S7, the postprocessing such as the image filter convolution and CT value conversion is applied to the back projection data D3 (x, y, z) to obtain a tomographic image D31 (x, y).

The image filter convolution processing in the postprocessing can be given as equation 8 below, assuming that the tomographic image after three-dimensional back projection is D31 (x, y, z), the data after image filter convolution is D32 (x, y, z), and the image filter is Filter (z).

[equation 6]

$$D32\,(x,y,z)=D31\,(x,y,z)*\text{Filter}\,(z) \quad \text{(equation 8)}$$

More specifically, the image filter convolution processing can be applied independently on each j row of the detector, so that the difference of the noise characteristics and the resolution characteristics for each row can be corrected.

The tomographic image thus obtained will be displayed on the monitor 6.

FIG. 7 shows a schematic flow diagram illustrating the details of the three-dimensional back projection processing (step S6 shown in FIG. 5).

In this preferred embodiment, the image to be image reconstructed is assumed to be three-dimensional image reconstructed along with the x-y plane, which is normal to the z-axis. The reconstruction area P is in parallel to x-y plane in the following description.

In step S61, projection data Dr in correspondence with each pixel of the reconstruction area P will be extracted from one single view within all views required for the tomographic image reconstruction (i.e., views for 360 degrees, or views of "180 degrees+fan angle").

Figure 8A:
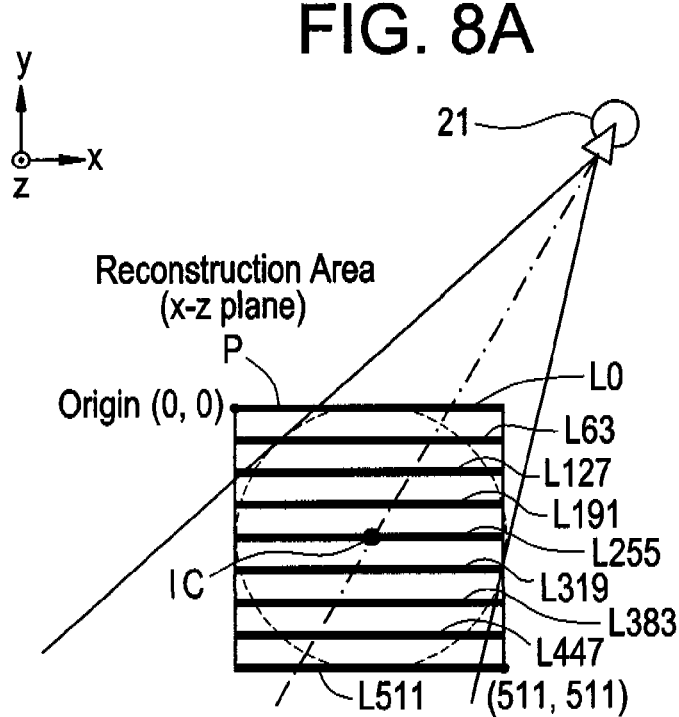
FIGS. 8a and 8b are schematic diagrams illustrating the projection of a line on the reconstruction area onto the X-ray transmission direction.
Figure 8B:
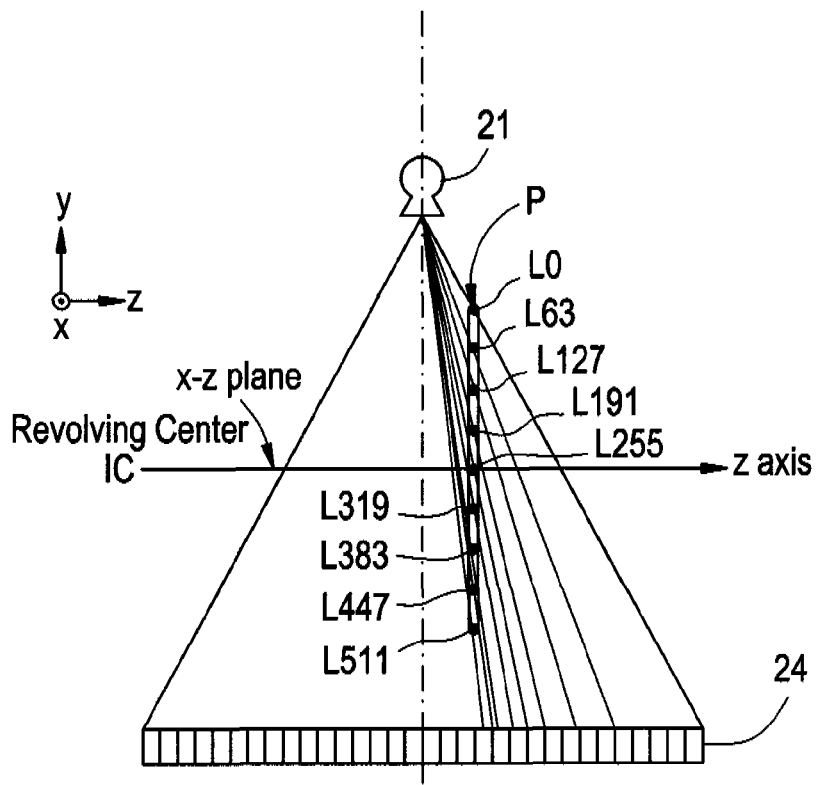
Figure 9:
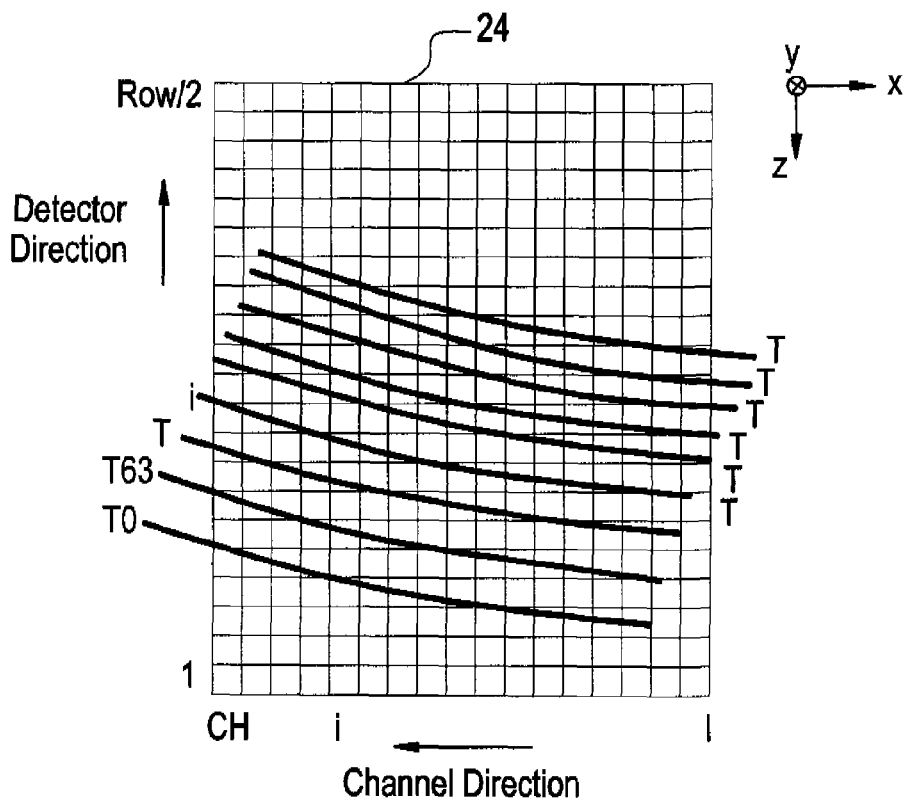
FIG. 9 is a schematic diagram illustrating the projected line on the reconstruction area.

As shown in FIG. 8(*a*) and FIG. 8(*b*), when the square area made of 512 pixels by 512 pixels in parallel to the x-y plane is defined as the reconstruction area P, the pixel row L0 that is in parallel to the x axis of y=0, pixel row L63 of y=63, pixel row L127 of y=127, pixel row L191 of y=191, pixel row L255 of y=255, pixel row L 319 of y=319, pixel row L 383 of y=383, pixel row L447 of y=447, pixel row L511 of y=511 are taken as rows, if the projection data on the lines T0 to T511 as shown in FIG. 9 that these pixel rows L0 to L511 are projected on the plane of the multi column X-ray detector 24 in the X-ray transmission direction, is extracted, then the data will be projection data Dr (view, x, y) of the pixel rows L0 to L511. Here x and y correspond to each pixel (x, y) of the tomographic image.

The X-ray transmission direction is defined by the geometrical position of the X-ray focal point of the X-ray tube 21 and each pixel and the multi column X-ray detector 24. As the z-axis coordinate z (view) of the X-ray detector data D0 (view, j, i) is known to be added in the X-ray detector data as the table translational moving z direction position Ztable (view), the X-ray transmission direction during acceleration and deceleration can be obtained correctly, in the data acquisition geometric system of the X-ray focal point and the multi column X-ray detector, including the X-ray detector data D0 (view, j, i) during acceleration and deceleration.

For example, when a part of a line is out of the channel direction of the multi column X-ray detector 24, namely the line T0 made by projecting the pixel row L0 on the plane of the multi column X-ray detector 24, the corresponding projection data Dr (view, x, y) is to be "0". If the line is out of the plane in the z direction, the projection data Dr (view, x, y) is to be determined by the extrapolation completion.

Figure 10:
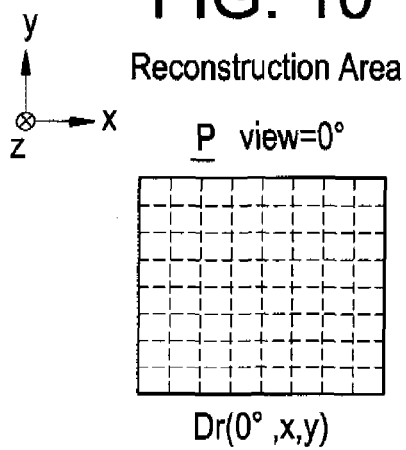
FIG. 10 is a schematic diagram illustrating the projection of the projection data Dr (view, x, y) on the reconstruction area.

As shown in FIG. 10, the projection data Dr (view, x, y) corresponding to each pixel of reconstruction area P can be extracted.

Figure 11:
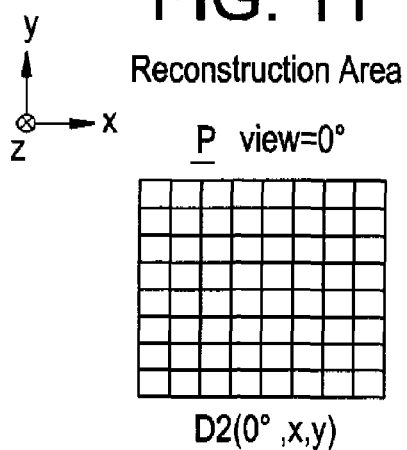
FIG. 11 is a schematic diagram illustrating the back projection pixel data D2 of each pixel on the reconstruction area.

Now back to FIG. 7, in step S62, the projection data Dr (view, x, y) is multiplied with the cone beam reconstruction weight coefficient to create the projection data D2 (view, x, y) as shown in FIG. 11.

The cone beam reconstruction weight coefficient w (i, j) is as follows. In case of the fan beam image reconstruction, in general, when view=βa, assuming that the straight line connecting the focal point of the X-ray tube 21 and the pixel g (x, y) on the reconstruction area P (on the x-y plane) has an angle γ with the center axis Bc of the X-ray beam, and the opposing view is view=βb, then the coefficient is given in the following equation 9.

[equation 7]

$$\beta b = \beta a + 180° - 2\gamma \quad \text{(equation 9)}$$

Assuming the angles with respect to the reconstruction area P made by the X-ray beam passing through the pixel g (x, y) on the reconstruction area P and the opposing X-ray beam are αa and αb respectively, the cone beam reconstruction weight coefficient ωa and ωb, relying on these angles, are multiplied then added to define the back projection pixel data D2 (0, x, y). In this case the data will be as in the following equation 10.

[equation 8]

$$D2\ (0, x, y) = \omega a \cdot D2\ (0, x, y)\_a + \omega b \cdot D2\ (0, x, y)\_b \quad \text{(equation 10)}$$

where D2 (0, x, y)_a is the back projection data of the view βa, and the D2 (0, x, y)_b is the back projection data of the view βb.

The sum of both opposing beams of the cone beam reconstruction weight coefficient will be as in the following equation 11.

[equation 9]

$$\omega a + \omega b = 1 \quad \text{(equation 11)}$$

By multiplying the cone beam reconstruction weight coefficient ωa and ωb then adding them, the cone angle artifact can be suppressed.

For example, for the cone beam reconstruction weight coefficient ωa and ωb, the coefficients given by the following equation can be used. Here ga designates to the weight coefficient of the view βa, and gb to the weight coefficient of the view βb.

When ½ of the fan beam angle is assumed to be γ max, then following equation 12 to equation 17 applies.

[equation 10]

$$ga = f(\gamma\ max, \alpha a, \beta a) \quad \text{(equation 12)}$$

$$gb = f(\gamma\ max, \alpha b, \beta a) \quad \text{(equation 13)}$$

$$xa = 2 \cdot ga^q / (ga^q + gb^q) \quad \text{(equation 14)}$$

$$xb = 2 \cdot gb^q / (ga^q + gb^q) \quad \text{(equation 15)}$$

$$wa = xa^2 * (3 - 2xa) \quad \text{(equation 16)}$$

$$wb = xb^2 * (3 - 2xb) \quad \text{(equation 17)}$$

(for example, q=1)

For example, as an example of ga and gb, max[ ] is assumed to be a function which takes the larger one of values, then the following equation 18 and equation 19 applies.

$$ga = \max[0, \{(\pi/2 + \gamma\ max) - |\beta a|\} \cdot |\tan(\alpha a)|] \quad \text{(equation 18)}$$

$$gb = \max[0, \{(\pi/2 + \gamma\ max) - |\beta b|\} \cdot |\tan(\alpha b)|] \quad \text{(equation 19)}$$

In case of the fan beam image reconstruction, the distance coefficient is multiplied to each pixel on the reconstruction area P. The distance coefficient will be $(r1/r0)^2$, where r0 is the distance from the focal point of the X-ray tube 21 to the detector row j, channel i of the multi column X-ray detector 24 corresponding to the projection data Dr, and r1 is the distance from the focal point of the X-ray tube 21 to the pixel on the reconstruction area P corresponding to the projection data Dr.

In case of the parallel beam image reconstruction, it is sufficient to multiply each pixel on the reconstruction area P with the cone beam reconstruction weight coefficient w (i, j).

Figure 12:
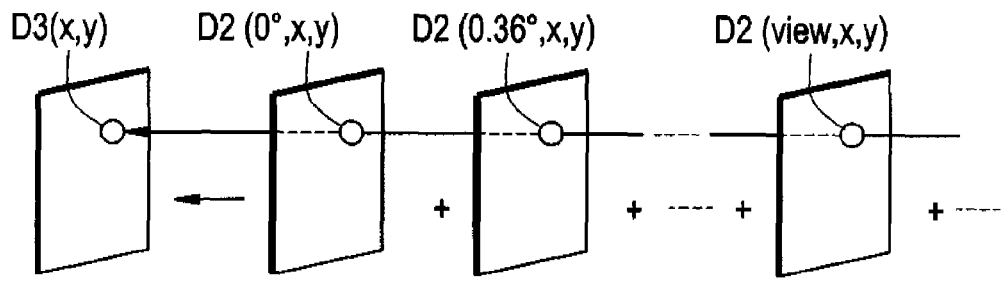
FIG. 12 is a schematic diagram illustrating how to obtain back projection data D3 by adding all view of the back projection pixel data D2 for each pixel.

In step S63, as shown in FIG. 12, the back projection data D3 (x, y) that is nullified in advance, is added with the project data D2 (view, x, y) for each pixel.

In step S64, steps S61 to S63 are iteratively repeated for all views required for the image reconstruction of the tomographic image (i.e., views for 360 degrees, or views of "180 degrees+fan angle") to obtain, as shown in FIG. 12, the back projection data D3 (x, y).

Figure 13A:
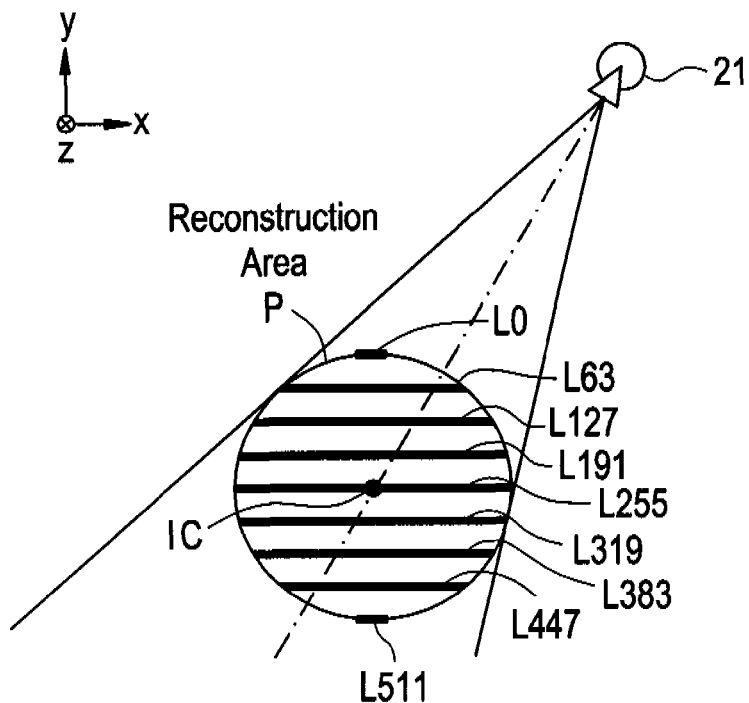
FIGS. 13a and 13b are schematic diagrams illustrating the projection of a line on the circular reconstruction area onto the X-ray transmission direction.
Figure 13B:
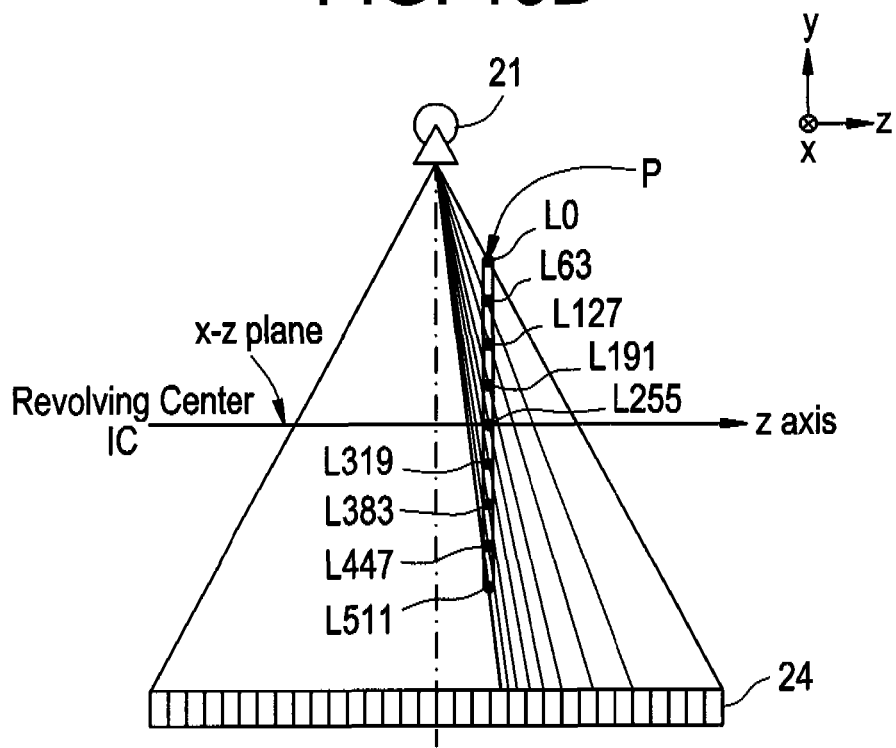

As shown in FIG. 13(*a*) and FIG. 13(*b*), the reconstruction area P may also be a circular area having the diameter of 512 pixels, instead of a square area of 512 pixels by 512 pixels.

In the medical X-ray CT, in general, the pixel value of the tomographic image is made to CT values, the CT values are values proportional to the X-ray absorption coefficient, that is standardized as air −1000, and water 0. The X-ray CT is regularly calibrated so as to maintain its accuracy.

Figure 16:
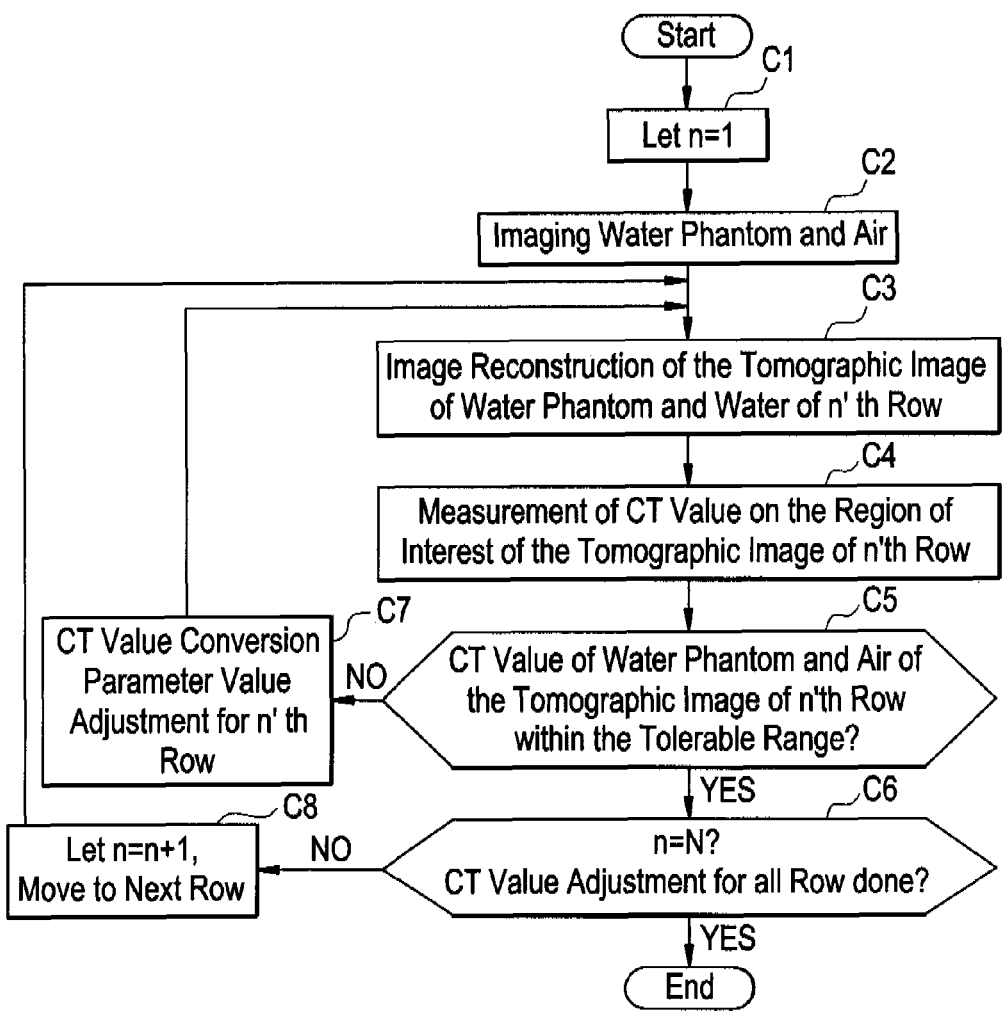
FIG. 16 is a schematic flow diagram of CT value adjustment.

In the conventional scan (axial scan) or the cinescan of an X-ray CT apparatus incorporating a multi column X-ray detector 24 with a cone angle not enough large, the flow of the CT value adjustment is as shown in FIG. 16. Here the multi column X-ray detector 24 is assumed to have N rows, and the CT value adjustment of the n'th row is to be done where $1 \leq n \leq N$.

In step C1, n=1.

In step C2, water phantom and air are imaged. In general the water phantom, having its diameter of 20 cm (corresponding to the diameter of a head) or about 30 cm (corresponding to the diameter of a chest), is a phantom made of an acrylic container filled with some water. The water phantom will be imaged to determine the CT value of the water. In addition, the CT value of air will also be determined by placing nothing in the imaging field.

In step C3, the image reconstruction of the tomographic image of the water phantom and air is performed for the n'th row.

When the value of CT value conversion parameters is modified and updated (step C7), the raw data of imaged water phantom or air is to be reconstructed again.

In step C4, The CT value of the region of interest of the tomographic image of n'th row, reconstructed in step C3, is measured. The region of interest is set to the tomographic image of n'th row among the tomographic images of water phantom and air, and the mean value of the CT values of each pixel of the tomographic images is determined from within the region of interest. In general, the region of interest is often determined as the circular region of an appropriate diameter at the center of the tomographic image. In addition to the center of the tomographic image, a plurality of regions of interest can be also set at the periphery of the tomographic image.

In step C5, it is determined whether the CT values of water phantom and air of the tomographic image of n'th row is within the allowable range. For the tomographic image of n'th row determined in step C4, it is determined whether the CT value of the water phantom in the region of interest is within the range of 0±ε 1, and whether the CT value of air in the region of interest is −1000±ε 2. Here, ε 1 and ε 2 are the tolerance error of the CT value of the water and air. If Yes, and the CT values of water and air are within the tolerance, then the process proceeds to step C6, and if No, and the CT values are not within the range then the process proceeds to step C7.

In step C6, it is determined whether n=N, and CT values of all rows are already adjusted. If Yes and the CT value adjustment of all rows is completed then the CT value adjustment is terminated. If No and the CT value adjustment of all rows is not yet terminated then the process goes to step C8.

In step C7, CT value conversion parameter of n'th row is adjusted and the process goes back to step C3.

In step C8, n=n+1. In other words the next row will be treated. Then the process will go back to step C3.

Figure 17:
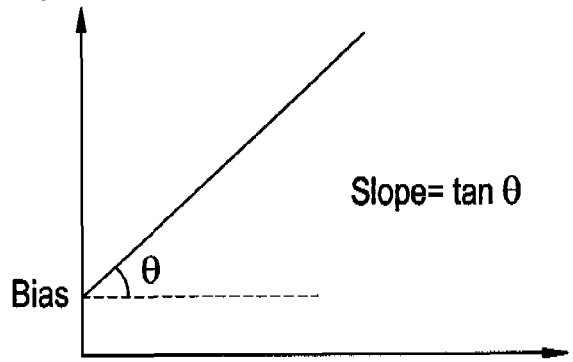
FIG. 17 is a schematic diagram illustrating the CT value conversion processing.

The CT value conversion parameter is determined by the bias and slope (=tan θ) as shown in FIG. 17, if the CT value conversion is to be performed in the first order conversion either by the CT value conversion prior to the back projection processing or by the CT value conversion after the back projection processing.

Figure 18:
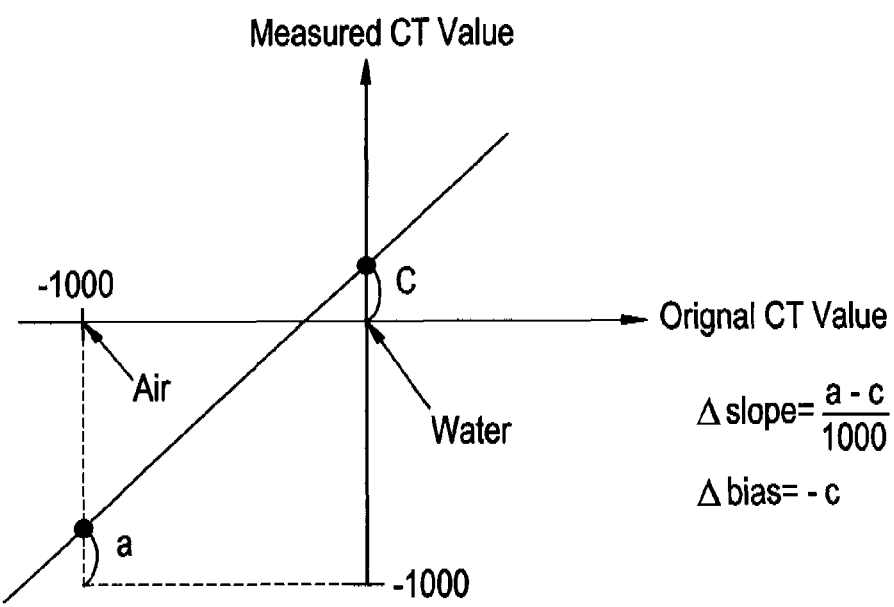
FIG. 18 is a schematic diagram illustrating the amount of modification of slope and bias with the amount of deviation of CT value.

An example of parameter modification method is shown in FIG. 18, when measuring actual CT values in the region of interest on the tomographic image and the value is deviated from the CT value of water, 0 or the CT value of air, −1000. In FIG. 18 the abscissa axis indicates the CT value of the raw material, and the ordinate axis indicates the actually measured CT value. In FIG. 18 the CT value of water is indicated to be b, and the CT value of air is indicated to be −1000+a.

In this case the modification amounts Δ bias, Δ slope of the CT value conversion parameters, bias, slope, will be given by the following equation 20 and equation 21.

[equation 12]

$$\Delta \text{slope} = \frac{a-c}{1000} \quad \text{(equation 20)}$$

$$\Delta \text{bias} = -c \quad \text{(equation 21)}$$

In the manner as described above, the CT value conversion parameters will be modified to converge the CT values to the water CT value 0 and air CT value −1000.

Figure 19:
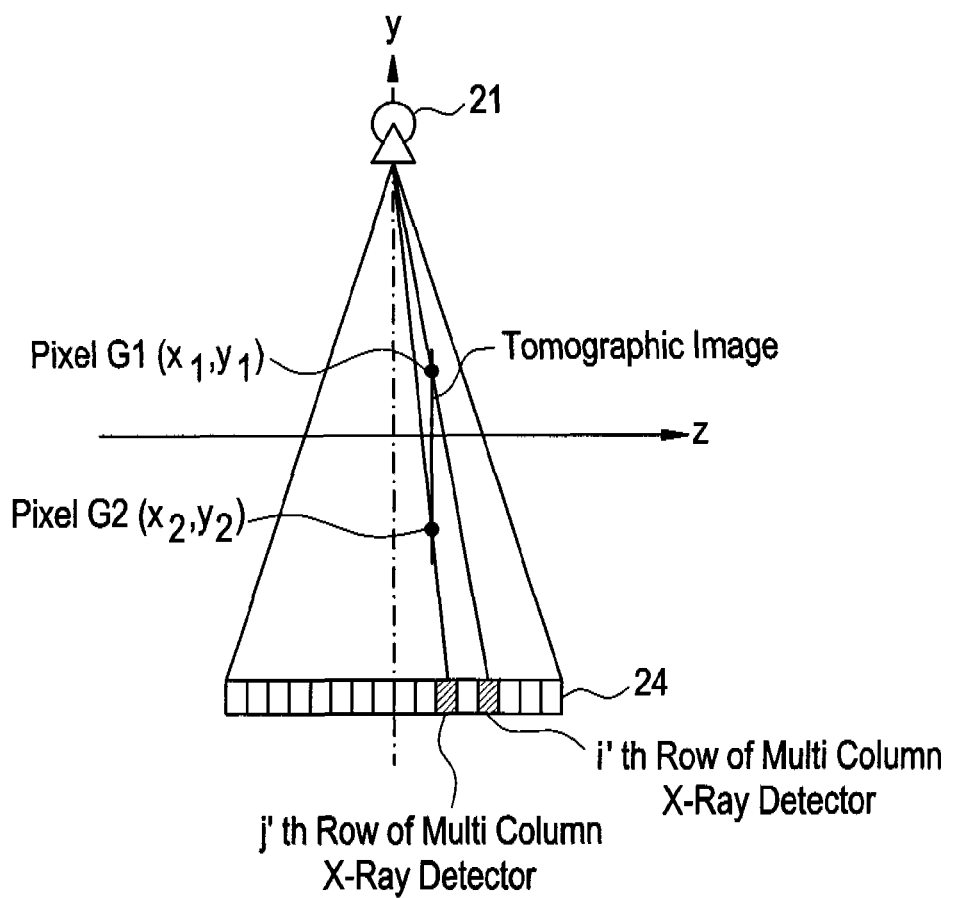
FIG. 19 is a schematic diagram illustrating the difference of corresponding detector row by the position of each pixel of a tomographic image.

When CT value conversion is done after the three-dimensional back projection processing, in the three-dimensional image reconstruction as described above, image will be reconstructed from the projection data of a plurality of rows of the two-dimensional X-ray area detector as shown in FIG. 19, and is not reconstructed from only one row of the two-dimensional X-ray area detector corresponding to the position in the x-axis direction of the tomographic image. For example, a pixel G1 (x1, y1) of a tomographic image G as shown in FIG. 19 will be reconstructed by using the data of the corresponding channel of i'th row of the multi column X-ray detector 24. Another pixel G2 (x2, y2) will be reconstructed by using the data of the corresponding channel of j'th row of the multi column X-ray detector 24.

Figure 20:
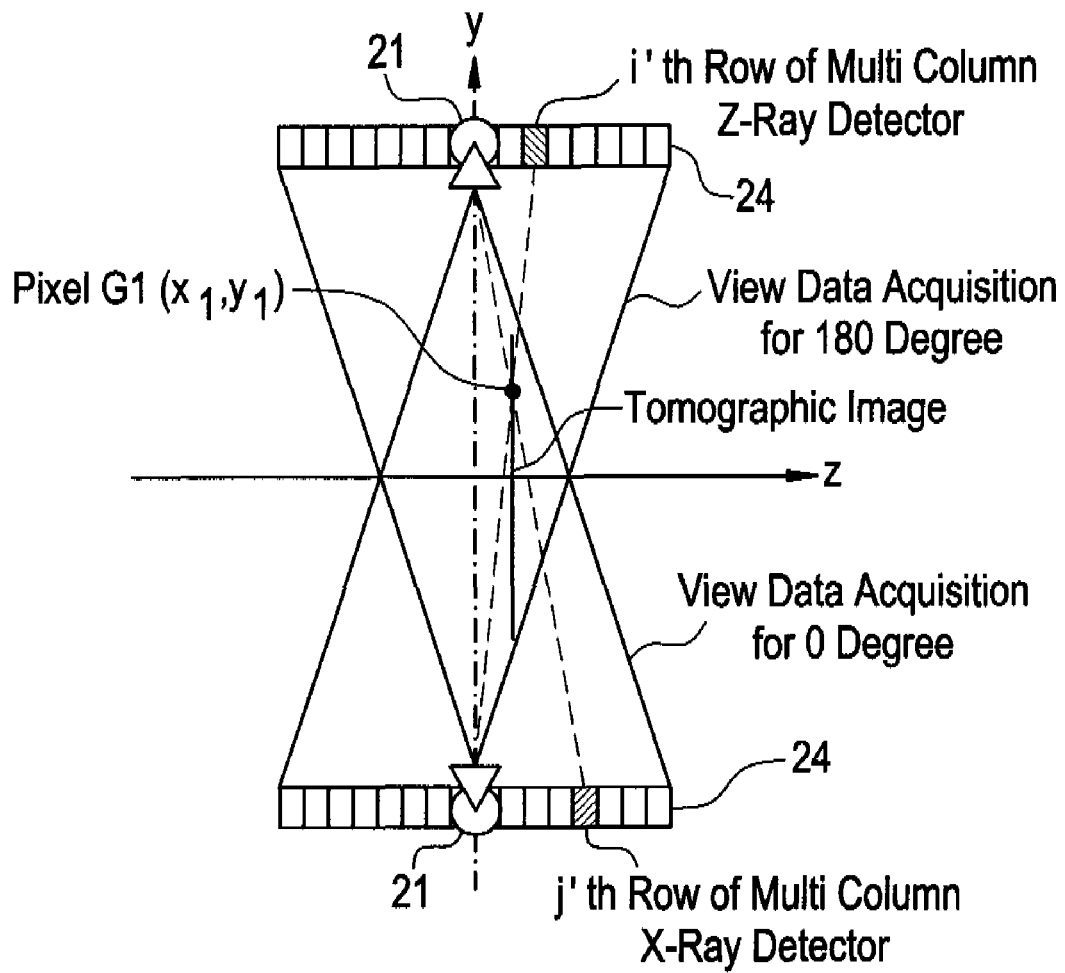
FIG. 20 is a schematic diagram illustrating the difference of corresponding detector row of the pixel of a tomographic image in each view.

As shown in FIG. 20, the row of two-dimensional X-ray area detector corresponding to the position on the x-y plane of the pixel of the tomographic image differs in each view. For instance, a pixel G1 (x1, y1) of a tomographic image G shown in FIG. 20 will be reconstructed by using the corresponding channel data of j'th row of the multi column X-ray detector 24 in the view data acquisition in the 0 degree angle direction. In the view data acquisition in the 180 degrees angle direction, it will be reconstructed by using the corresponding channel data of i'th row of the multi column X-ray detector 24. Because of this the CT value is converted preferably by the CT value adjustment parameter of the row of the two-dimensional X-ray area detector corresponding to the position on the x-y plane of each pixel of the tomographic image in each view. Thus the contribution rate of the CT value adjustment parameter of each row to each pixel of the tomographic image, when the data acquisition system comprised of the X-ray tube 21 and the multi column X-ray detector 24 revolves one turn, will be different by relying on the position in the x-y plane of the pixel, the position in the z-direction of the tomographic image, position of the X-ray focal point, and the position of each row of the two-dimensional X-ray area detector. Therefore the CT value adjustment parameters of the tomographic image can be determined by taking into account this contribution rate.

In an X-ray CT apparatus using a multi column X-ray detector 24 of wider X-ray detector width in z direction or a two-dimensional X-ray area detector 24, three-dimensional back projection processing is used for the image reconstruction in order to improve the image quality, as well as decrease the artifacts.

The flow of CT value adjustment in this case will be as shown in FIG. 23. The multi column X-ray detector 24 is assumed to have N rows as similar to FIG. 16, and the CT value adjustment of n'th row is performed where $1 \leq n \leq N$.

In steps C11, C12, C13, C14, C15, C16, C18, the process flow is the same as the steps C1, C2, C3, C4, C5, C6, C8 of FIG. 16.

In step C17, the value of the CT value conversion parameter which affects the CT value of each pixel of the tomographic image at the position of n'th row will be modified. For instance the rows contributing to a pixel Gi (xi, yi) in the region of interest having its CT value measured are two, namely the n'th row and n+1'th row of the multi column X-ray detector 24, and the contribution rate of each is $W_n$, $W_{n+1}$, respectively. The equation 22 should be satisfied at this time.

[equation 13]

$$W_n + W_{n+1} = 1 \quad \text{(equation 22)}$$

The amount of modification of the bias and slope are designated to Δ bias and Δ slope, respectively. For the CT value conversion parameters of n'th row the amount of modification as stated below are added to the bias and slope.

In a similar manner for the CT value conversion parameters of n+1'th row, for example, the amount of modification as stated below will be added.

[equation 14]

$$W_{n+1} \cdot \Delta \text{bias}, W_{n+1} \cdot \Delta \text{slope} \quad \text{(equation 23)}$$

Since the contribution rate $W_n$ and $W_{n+1}$ differs for each pixel, the amount of modification of the CT value conversion parameters may be determined for a plurality of pixels within the region of interest. In case in which the region of interest to measure the CT value is present not only in the center but also in the periphery of the tomographic image, the CT value differs in correspondence with the position of each in the tomographic image, and the contribution rate to each row of the multi column X-ray detector 24 also differs, so that for each pixel of the region of interest, the amount of modification may be added to each row of the multi column X-ray detector 24 to which contributes each pixel.

In case of helical scan, the contribution row differs for every position of each pixel, so that for each pixel of the region of interest, the amount of modification may be added to each row of the multi column X-ray detector 24 to which contributes each pixel of the region of interest.

If the CT value conversion is performed before the three-dimensional back projection processing, the processing will be simpler when compared to the case after the three-dimensional back projection processing, in which case after the preprocessing of the step S2 or after the beam hardening correction of step S3, or before the reconstruction function convolution of step S5, the projection data will be normalized only with the bias and slope of the first order conversion for example, to decrease the dispersion.

The CT value conversion may be performed before the back projection processing, or the CT value conversion may be performed after the back projection processing, and in any case the CT value conversion of the tomographic image can be performed more correctly with less affection due to the dispersion of the sensitivity of each row of the X-ray detector, incoming dose of X-ray, or quality of X-ray, and the like.

In the X-ray CT apparatus 100 as have been described above, in accordance with the X-ray CT apparatus or X-ray CT imaging method of the present invention, the present invention has the effect of achieving an X-ray CT imaging method or X-ray CT apparatus which allows appropriate CT value conversion in a conventional scan (axial scan) or cinescan or helical scan by an X-ray CT apparatus having a multi column X-ray detector or a two-dimensional area X-ray detector of matrix arrangement represented by a flat panel X-ray detector.

The image reconstruction method may also be the three-dimensional image reconstruction method according to the feldkampf method that is well known in the art. Furthermore the image reconstruction may be any one of known three-dimensional image reconstruction methods.

In the preferred embodiment, although the difference of image quality due to the difference of X-ray cone angle and the like is adjusted in particular in the conventional scan (axial scan) by convoluting the row direction (z direction) filter having different coefficient for each row to achieve the image quality of uniform slice thickness, artifact, and noise in every row, a variety of filter coefficients can be applicable thereto. The similar effect can be achieved in any case.

Also in the preferred embodiment the first order conversion is used for the CT value conversion, the similar effect may be achieved by using the second order conversion, the third order conversion, and so on.

The present invention may be applicable not only to the medical X-ray CT apparatus, but also to the industrial X-ray CT apparatus, or to the X-ray CT-PET apparatus, X-ray CT-SPECT apparatus in combination with another apparatus.

The invention claimed is:

1. An X-ray CT apparatus comprising:
    an X-ray data acquisition device configured to acquire X-ray projection data of an X-ray passed through a subject positioned between an X-ray generator and an opposite multi-row X-ray detector;
    a CT value adjustment device configured to obtain CT value conversion parameters with respect to each detector row of said multi-row X-ray detector, the CT value conversion parameters used in a CT value conversion process for normalizing CT values of the projection data; and
    an image reconstruction device configured to reconstruct a tomographic image from the projection data acquired by said X-ray data acquisition device using a three-dimensional back projection process in which the projection data acquired by said multi-row X-ray detector is used to reconstruct the tomographic image, said image reconstruction device further configured to perform the CT value conversion process to the projection data using the CT value conversion parameters prior to a three-dimensional back projection process.

2. An X-ray CT apparatus according to claim 1, wherein said image reconstruction device is configured to perform the CT value conversion process after a reconstruction function convolution process.

3. An X-ray CT apparatus according to claim 1, wherein said image reconstruction device is configured to perform the CT value conversion process to the projection data by using the CT value conversion parameters prior to a reconstruction function convolution process and after pre-processing.

4. An X-ray CT apparatus according to claim 1, wherein the CT value conversion parameters are determined based on a contribution rate of the projection data of each detector row of said multi-row X-ray detector to each pixel in the tomographic image.

5. An X-ray CT apparatus comprising:
    an X-ray data acquisition device configured to acquire X-ray projection data of an X-ray passed through a subject positioned between an X-ray generator and an opposite multi-row X-ray detector;
    a CT value adjustment device configured to obtain CT value conversion parameters with respect to each detector row of said multi-row X-ray detector based on a contribution rate of the projection data of each detector row to each pixel in a tomographic image, the CT value conversion parameters used in a CT value conversion process for normalizing CT values of the projection data; and
    an image reconstruction device configured to reconstruct the tomographic image from the projection data acquired by said X-ray data acquisition device using a three-dimensional back project ion process in which the projection data acquired by said multi-row X-ray detector is used to reconstruct the tomographic image, said image reconstruction device further configured to perform a CT value conversion process to the projection data by using the CT value conversion parameters after a three-dimensional back projection process.

6. An X-ray CT apparatus according to claim 5, wherein the contribution rate of the projection data of each detector row of said multi-row X-ray detector is determined by a position of an X-ray focus, a position of each detector row of said multi-row X-ray detector, a position on an x-y plane of each pixel of the tomographic image, and a z-axis coordinate position on the tomographic image, wherein a revolving plane of said X-ray data acquisition device is defined as the x-y plane, and a moving direction of an imaging table which is perpendicular to the x-y plane is defined as a z direction.

7. An X-ray CT apparatus according to claim 5, wherein the contribution rate of the projection data of each detector row of said multi-row X-ray detector is determined by a helical pitch and a z-axis coordinate position on the tomographic image in a helical scan.

8. An X-ray CT imaging method comprising the steps of:
    acquiring X-ray projection data of an X-ray passed through a subject positioned between an X-ray generator and an opposite multi-row X-ray detector having a plurality of detector rows; and
    reconstructing a tomographic image from the projection data by executing a CT value conversion process for converting the projection data using CT value conversion parameters to normalize CT values of the projection data, the CT conversion parameters obtained with respect to each detector row of the plurality of detector rows, and using a three-dimensional back projection process in which projection data acquired by the plurality of detector rows is used to reconstruct the tomographic image.

9. An X-ray CT imaging method according to claim 8, wherein reconstructing a tomographic image comprises performing a CT value conversion process after a reconstruction function convolution step.

10. An X-ray CT imaging method according to claim 8, further comprising converting the projection data of the tomographic image to CT values prior to a reconstruction function convolution process and after pre-processing.

11. An X-ray CT imaging method according to claim 10, wherein converting the projection data of the tomographic image to CT values comprises determining the CT value conversion parameters by taking into account the contribution rate of the projection data from each detector row to each pixel in a tomographic image.

12. An X-ray CT imaging method comprising the steps of:
acquiring X-ray projection data of an X-ray passed through a subject positioned between an X-ray generator and an opposite multi-row X-ray detector including a plurality of detector rows;
reconstructing a tomographic image from the projection data using a three-dimensional back projection process in which the projection data from the plurality of detector rows is used to reconstruct the tomographic image; and
performing a conversion process on the tomographic image data after the three-dimensional back projection process, the conversion process based on CT value conversion parameters used for normalizing CT values of the projection data, the CT value conversion parameters obtained with respect to each detector row of the plurality of detector rows based on a contribution rate of the projection data of each detector row to each pixel in the tomographic image.

13. An X-ray CT imaging method according to claim 12, further comprising determining the contribution rates based on, a position of an X-ray focus, a position of each detector row of the plurality of X-ray detector rows, a position on an x-y plane of each pixel of the tomographic image, and a z-axis coordinate position on the tomographic image, wherein a revolving plane of the X-ray generator and the X-ray detector is defined as the x-y plane, and a moving direction of an imaging table which is perpendicular to the x-y plane is defined as a z direction.

14. An X-ray CT imaging method according to claim 12, further comprising determining contribution rates based on a helical pitch and a z-axis coordinate position on the tomographic image in a helical scan.

* * * * *

UNITED STATES PATENT AND TRADEMARK OFFICE
CERTIFICATE OF CORRECTION

| | | |
|---|---|---|
| PATENT NO. | : 7,492,854 B2 | Page 1 of 1 |
| APPLICATION NO. | : 11/557716 | |
| DATED | : February 17, 2009 | |
| INVENTOR(S) | : Nishide et al. | |

It is certified that error appears in the above-identified patent and that said Letters Patent is hereby corrected as shown below:

In Column 20, Line 17, in Claim 5, delete "project ion" and insert -- projection --, therefor.

Signed and Sealed this

Sixteenth Day of March, 2010

David J. Kappos
*Director of the United States Patent and Trademark Office*